United States Patent
Zon et al.

(10) Patent No.: US 6,524,833 B1
(45) Date of Patent: Feb. 25, 2003

(54) TWO STERILE-20 KINASE-LIKE PROTEINS AND METHODS OF USE THEREOF

(75) Inventors: Leonard I. Zon, Wellesley, MA (US); Sadhana Agarwal, Cambridge, MA (US); Jennifer Best, Cambridge, MA (US); Brenda Vail, Dedham, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/685,462

(22) Filed: Oct. 10, 2000

Related U.S. Application Data

(63) Continuation-in-part of application No. 09/591,083, filed on Jun. 9, 2000, which is a continuation of application No. PCT/US98/26116, filed on Dec. 9, 1998.
(60) Provisional application No. 60/069,078, filed on Dec. 9, 1997.

(51) Int. Cl.[7] ........................... C12N 9/12; C12N 15/00; C12N 5/00; C12N 1/20; C07H 21/04

(52) U.S. Cl. .................. 435/194; 435/252.3; 435/320.1; 435/325; 435/6; 536/23.2

(58) Field of Search ............................. 435/194, 252.3, 435/320.1, 325, 6; 536/23.2

(56) References Cited

U.S. PATENT DOCUMENTS

| | | | |
|---|---|---|---|
| 5,518,911 A | 5/1996 | Abo et al. | 435/194 |
| 5,605,825 A | 2/1997 | Abo et al. | 435/194 |

FOREIGN PATENT DOCUMENTS

| | | |
|---|---|---|
| WO | WO97/42212 | 11/1997 |

OTHER PUBLICATIONS

Database EST, Accession No. AA200915, Feb. 1997.*
Database EST, Accession No. AA285799, Apr. 1997.*
Dan et al., Trends in Cell Biology, 11(5), 220–230, 2001.
Coso, O. A., et al., "The Small GTP–Binding Proteins Rac1 and Cdc42 Regulate the Activity of the JNK/SAPK Signaling Pathway," Cell, 81: 1137–1146 (1995).
Nobes, C.D., and Hall, A., Rho, Rac, and Cdc42 GTPases Regulate the Assembly of Multimolecular Focal Complexes Associated With Actin Stress Fibers, Lamellipodia, and Filopodia, Cell, 81: 53–62 (1995).
Ridley, A.J., et al., "The Small GTP–Binding Protein rac Regulates Growth Factor–Induced Membrane Ruffling," Cell, 70: 401–410 (1992).
Rouse, J., et al., "A Novel Kinase Cascade Triggered by Stress and Heat Shock That Stimulates MAPKAP Kinase–2 and Phosphorylation of the Small Heat Shock Proteins," Cell, 78:1027–1037 (1994).
Dérjard, B., et al., "JNK1: A Protein Kinase Stimulated by UV Light and Ha–Ras That Binds and Phosphorylates the c–Jun Activation Domain," Cell, 76: 1025–1037 (1994).
Minden, A., et al., "Selective Activation of the JNK Signaling Cascade and c–JUn Transcriptional Activity by the Small GTPases Rac and Cdc42HS," Cell, 81: 1147–1157 (1995).
Lee, J.C., et al., "A Protein Kinase Involved in the Regulation of Inflammatory Cytokine Biosynthesis," Nature, 372: 739–746 (1994).
Kyriakis, J.M., et al., "The Stress–Activated Protein Kinase Subfamily of c–Jun Kinases," Nature, 369: 156–160 (1994).
Pombo, C.M., et al., "Activation of the SAPK Pathway by the Human STE20 Homologue Germinal Centre Kinase," Nature, 377: 750–754 (1995).
Olson, M.F., et al., "An Essential Role for Rho, Rac, and Cdc42 GTPases in Cell Cycle Progression Through $G_1$," Science, 269: 1270–1272 (1995).
Minden, A., et al., "Differential Activation of ERK and JNK Mitogen–Activated Protein Kinases by Raf–1 and MEKK," Science, 266: 1719–1723 (1994).
Ramer, S.W., and Davis, R.W., "A Dominant Truncation Allele Identifies A Gene, STE20, That Encodes a Putative Protein Kinase Necessary for Mating in Saccharomyces cerevisiae," Proc. Natl., Acad. Sci. USA, 90: 452–456 (1993).
Brzeska, H., et al., "p21–Activated Kinase Has Substrate Specificity Similar to Acanthamoeba Myosin I Heavy Chain Kinase and Activates Acanthamoeba Myosin I," Proc. Natl. Acad. Sci. USA, 94: 1092–1095 (1997).
Davis, R.J., "MAPKs: New JNK Expands the Group," Trends in Biochemical Sciences, 19: 470–473 (1994).
Nishida, E., and Gotoh, Y., "The MAP Kinase Cascade is Essential for Diverse Signal Transduction Pathways," Trends in Biochemical Sciences, 18:128–131 (1993).
Clerk, A., and Sugden, P.H., "Activation of p21–Activated Kinase α (αPAK) by Hyperosomotic Shock in Neonatal Ventricular Myocytes," Federation of European Biochemical Societies Letters, 403: 23–25 (1997).
Creasy, C.L. and Chernoff J., "Cloning and Characterization of A Human Protein Kinase with Homology to Ste20," The Journal of Biological Chemistry, 270: 21695–21700 (1995).
Herskowitz, I., "MAP Kinase Pathways in Yeast: For Mating and More," Cell, 80: 187–197 (1995).
Itoh, S., et al., "Molecular Cloning and Characterization of a Novel Putative STE20–Like Kinase in Guinea Pigs," Archives of Biochemistry and Biophysics, 340: 201–207 (1997).
Knaus, U.G., et al., Regulation of Human Leukocyte p21–Activated Kinases Through G Protein–Coupled Receptors, Science, 269: 221–223 (1995).
Leeuw, T., et al., "Pheromone Response in Yeast: Association of Bem1p with Proteins and the MAP Kinase Cascade and Actin," Science, 270: 1210–1213. (1995).

(List continued on next page.)

Primary Examiner—M. Monshipouri
(74) Attorney, Agent, or Firm—Hamilton, Brook, Smith & Reynolds, P.C.

(57) ABSTRACT

Described herein are novel members of the Sterile 20 family of serine/threonine protein kinases, including nucleic acid sequences and amino acid sequences.

6 Claims, 10 Drawing Sheets

OTHER PUBLICATIONS

Lian, J.P., and Badway, J.A., "Activation of the p21–Activated Protein Kinases from Neutrophils with an Antibody that Reacts with the N–Terminal Region of Pak 1," *Federation of European Biochemical Societies Letters,* 404:211–215 (1997).

Lu, W., et al., "Activation of Pak by Membrane Localization Mediated by an $SH_3$ Domain from the Adaptor Protein Nck," *Current Biology,* 7: 85–94 (1997).

Manser, E., et al., "Expression of Constitutively Active α–PAK Revelas Effects of the Kinase on Actin and Focal Complexes," *Molecular and Cellular Biology,* 17: 1129–1143 (1997).

Manser, E., et al., "Molecular Cloning of a New Member of the p21–Cdc42/RAC–Activated Kinase (PAK) Family," *The Journal of Biological Chemistry, 270: 25070–25078 (1995).*

Manser, E., et al., "A Brain Serine/Threonine Protein Kinase Activated by Cdc42 and Rac1," *Nature,* 367: 40–46 (1994).

Martin, H., et al., "Characterization of SKM1, a *Saccharomyces Cerevisiae* Gene Encoding a Novel Ste20/PAK–Like Protein Kinase," *Molecular Microbiology,* 23: 431–444 (1997).

Osada, S., et al., "YSK1, a Novel Mammalian Protein Kinase Structurally Related to Ste20 and SPS1, but is not Involved in the Known MAPK Pathways," *Department of Molecular Biology, Yokohama City University School of Medicine,* pp. 2048–2057 (1997).

Sells, M.A. and Chernoff, J., "Emerging from the Pak: the p21–Activated Protein Kinase Family," *Cell Biology,* 7: 162–167 (1997).

Simon, M., et al., "Role for the Rho–Family GTPase Cdc42 in Yeast Mating–Pheromone Signal Pathway," *Nature,* 376: 702–705 (1995).

Su, Y., et al., "NIK is a New Ste20–Related Kinase that Binds NCK and MEKK1 and Activates the SAPK/JNK Cascade Via a Conserved Regulatory Domain," *The EMBO Journal,* 16: 1279–1290 (1997).

Tung, R.M. and Blenis, J., "A Novel Human SPS1/STE20 Homologue, KHS, Activates Jun N–Terminal Kinase," *Oncogene,* 14: 653–659 (1997).

Yu, W., et al., "Isolation and Characterization of a Structural Homologue of Human PRK2 from Rat Liver," *The Journal of Biological Chemistry,* 272: 10030–10034 (1997).

Schinkmann, K., and Blenis, J., "Cloning and Characterization of a Human STE20–Like Protein Kinase with Unusual Cofactor Requirements," *The Journal of Biological Chemistry,* 272: 28695–28703 (1997).

Friesen, H., et al., "Mutation of the SPS1–Encoded Protein Kinase of *Saccharomyces Cerevisiae* Leads to Defects in Transcription and Morphology During Spore Formation," *Genes and Development,* 8: 2162–2175 (1994).

Kozma, R., et al., "The Ras–Related Protein Cdc42Hs and Bradykinin Promote Formation of Peripheral Actin Microspikes and Filopodia in Swiss 3T3 Fibroblasts," *Molecular and Cellular Biology,* 15: 1942–1952 (1995).

Marshall, C.J., "MAP Kinase Kinase Kinase, MAP Kinase Kinase and MAP Kinase," *Current Opinion in Genetics and Development,* 4: 82–89 (1994).

Leberer, E., et al., "The Protein Kinase Homologue Ste20p is Required to Link the Yeast Pheromone Response G–Protein βγ Subunits to Downstream Signalling Components," *The EMBO Journal,* 11: 4815–4824 (1992).

Martin, G.A., et al., "A Novel Serine Kinase Activated by Rac1/CDC42Hs–Dependent Autophosphorylation is Related to PAK65 and STE20," *The EMBO Journal,* 14: 1970–1978 (1995).

Bagrodia, S., et al., "Identification of a Mouse $p21^{Cdc42/Rac}$ Activated Kinase," *The Journal of Biological Chemistry,* 270: 22731–22737 (1995).

Puri, P., et al., "Induction of Terminal Differentiation by Constitutive Activation of p38 MAP Kinase in Human Rhabdomyosarcoma Cells," *Genes and Development,* 14: 574–584 (2000).

Marra, M., et al., "vx21d04.r1 Soares 2NbMT Mus Musculus cDNA Clone 1265095 5' Similar to TR: 014840 014840 STE20–Like Kinase 3,"Database EMBL—EMEST4, Entry/Acc. No. Aa881667 (1998).

Hillier, L., et al., "zb05e11.r1 Soares Fetal Lung NbHL19W Homo Sapiens cDNA Clone 301196 5' Similar to SW: KPAK_RAT P35465 Serine/Threonine–Protein Kinase Pak," Database EMBL—EMEST13, Entry HS504336, Acc. No. W16504 (1996).

* cited by examiner

C12-2bs. Length: 1500

```
   1 ctagtcgggc ctgccgggca tgcagaacct gaaagcagac ccagaagagc
  51 tttttaccaa gctagagaag attggaaagg gctctttttgg tgaagtgttc
 101 aaaggcattg acaatcggac tcagaaagtg gtggccataa aaatcattga
 151 tctggaagaa gccgaggacg agatagagga catccaacaa gagatcacag
 201 tgctgagcca gtgtgacagt ccctacgtca ccaagtacta tggatcctat
 251 ctcaaggata ctaagttgtg gataatcatg gagtatcttg gtggaggctc
 301 tgccctggat ctgttagagc ctggcccttt agatgaaatt cagattgcaa
 351 ccatattacg agaaattctg aaaggacttg attatctaca ctcggagaag
 401 aaaattcaca gagatattaa agaggccaat gttctgctct ctgaacatgg
 451 agaggtgaag ctggcagact ttggagtggc cggccagctg acggataccc
 501 agatcaaaag gaacaccttc gtgggtaccc cttctggat ggcgccggag
 551 gtcatcaagc agtcagccta cgactcaaag gcagacatct ggtcccttgg
 601 catcaccgca atagaactgg ccaaggaga gccaccacat tctgagctgc
 651 acccatgaa ggtgttattc ctcatcccaa agaacaaccc tcccacactg
 701 gaagggaact acagcaaacc cctcaaggag ttcgtggagg cctgcctgaa
 751 caaggagccc agctttaggc ccactgctaa ggaattattg aagcacaaat
 801 tcataatccg caatgcaaag aaaacgtcct acttgaccga gcttatcgac
 851 aggtacaaga ggtggaaggc ggagcagagc cacgaggact ccagctcgga
 901 ggactctGAC GTGGAGACAG ATGGCCAGGC GTCTGGAGGC AGCGACTCTG
 951 GGGACTGGAT CTTCACTATC CGGGAGAAAG ATCCCAAGAA TCTGGAGAAC
1001 GGAACTCTTC AGCTCTCGGA CTTGGAAAGA AATAAGATGA AAGATATCCC
1051 AAAGAAGCCT TTCTCTCAGT GTTTTATCCC ACAATCATTT CTCCTCCTGT
1101 TTTGCGGAGC TGAAAAGACA AAGAGCCAAG GCATGCGGAG GGAACTTGGG
1151 GTCAATAGAA GAGCTGCGGG GGAGCCATCT ACTTGGCGGA AGAGGCCTGC
1201 CCTGGGATCT CAGACACTAT GGTGGCACAG CTTGTGCAGC GGCTGCAGAG
1251 ATATTCTCTG AGTGGCGGAG GAGCCTCAGC GCACTGAAGG CCCATGGCGC
1301 CCGGGTTGGT TTTTCCTTTC TTCTTCATCT TCCTTCTTTT TAAAAGTCAA
1351 CGAGAGCCTT TGCCGACTCT GCGAAGAGGT GTCACGGAGG GGCCCACCCG
1401 CCCTCCCATA GCGCCGGCAC CTGTCCCTCG TGCCGAATTC CTGCAGCCCG
1451 GGGGATCCAC TAGTTCTAGA GCGGCCGCCA CCGCGGTGGA GCTCCAGTTT
```

Fig. 1

5e.New Length: 1979

```
   1 GGCACGAGCC CAGGTCCCAG GCACCGCCAC AGGTCAAGCC CTGCATTCAG
  51 GAAAGAGAGC AACACTGCAG TTAGCCAAAA GCCAGGCAGG CGAGCGGCAT
 101 AGAGGCCTCG ATCGAGAAGC CCGGTAGAGC TGCAGAGATA CCTCCGTAGG
 151 AGGAGCCAGT CTCTGCCGGA GGCGCCACCG CCACCACCGC AGAAGCAGCG
 201 CGAAGTAGCA GTCGCCACCA TGGCCCACTC ACCGGTGGCT GTTCAAGTGC
 251 CTGGGATGCA GAATAATATA GCAGATCCAG AAGAACTGTT CACAAAATTA
 301 GAGCGCATTG GAAAAGGCTC CTTTGGAGAA GTTTTCAAAG GAATTGATAA
 351 CCGTACTCAG CAAGTGGTTG CAATTAAAAT CATTGACCTT GAGGAAGCTG
 401 AGGATGAAAT AGAAGACATC AACAAGAAA TAACTGTTT GAGTCAGTGC
 451 GACAGCTCAT ATGTAACAAA ATACTATGGG TCCTATTTAA AGGGTTCAAA
 501 ACTATGGATA ATAATGGAAT ACCTAGGTGG AGGTTCAGCA TTGGATCTTC
 551 TGCGTGCTGG TCCATTTGAT Gagttccaga ttgccaccat gctcaaggag
 601 attttgaaag gtctggacta tctacattct gaaagaaaa tccaccgaga
 651 cattaaagct gCcaacgtct tgctttcaGA ACAAGGTGAT GTTAAACTGG
 701 CTGACTTTGG AGTTGCTGGC CAGCTGACAG ATACACAAAT CAAAAGAAAC
 751 ACCTTCGTAG GGACTCCGTT Ttggatggct cctgaagtta ttcaacagtc
 801 agcttatgac tctaaagctg acatatggtc tttgggaatt actgctattg
 851 aacttgccaa gggagagcct Ccgaattctg acatgcatcc aatgagagtt
 901 ctGTTTCTTA TTCCAAAAAA CAACCCTCCA ACTCTTATTG GAGACTTTAC
 951 TAAGTCTTTC AAGGAGTTTA TTGATGCTTG CCTGAATAAA GACCCGTCAT
1001 TTCGTCCTAC AGCTAAAGAA CTTTTGAAGC ATAAGTTCAT CGTAAAAAAT
1051 TCAAAGAAGA CTTCTTATCT GACTGAATTG ATCGATCGAT TTAAGAGATG
1101 GAAGGCAGAA GGCCACAGTG ATGAGGAATC TGATTCCGAG GGCTCTGACT
1151 CGGAATCCAG CAGCAGGGAA AGTAACCCTC ACCCTGAATG GAGTTTCACC
1201 ACTGTGCGTA AGAAGCCTGA TCCAAAGAAA CTGCAGAATG GGAAGAGCA
1251 AGATCTTGTG CAAACCTTGA GCTGTTTGTC TATGATAATC ACACCTGCAT
1301 TTGCCGAACT TAAACAGCAG GACGAGAATA ATGCGAGTCG AAACCAGGCA
1351 ATTGAAGAAC TTGAGAAAAG TATTGCTGTG CTGAAACCG CCTGTCCTGG
1401 CATCACAGAT AAGATGGTGA AGAAACTAAT CGAAAAATTT CAAAAGTGTT
1451 CTGCGGATGA ATCCCCTTAA GAAATCTGTT GTCATTACTT TTGGCTTCTG
```

Fig. 2A

```
1501  TTTCATGTGG ACCAGGAGAA ACCCACCAAA GCTATGTCAA CCTTATAAAT
1551  GCTTAACTCA TGAGCTCCAT GTgccttttg gatctttgcc acattgaaga
1601  tttagaggaa gctattaaac tattttgtga tggtgattat cattttgtat
1651  tttaaagaga ttattttgta aggaataatt ttaatactat agttttgccg
1701  gtattgtagt aaatgctgag atacaggttt tttgtttttt gttttttaat
1751  tttaggtacC AtTAtTTCtT ATGtTCATgG aATGaATACT GtTTgGtTTg
1801  GaATCtTTAG TTAACTGTAT ACTCATaAAC ATACAGGTCt TTCAAAGTCA
1851  TCCTAACTAT TAAATGTtTG TAAATCATCA AGCTtCAAAA agCAtTCttt
1901  ttCCCCcaca caagtatatt ctaaaaagac tatttgtaat gaggtggaag
1951  taagtaatac cttcttaaaa cctcgtgcc
```

Fig. 2B

SEQ ID No. 5:

5'  ATA GGA TCC CA(CT) (AC)G(AGCT) GA(AT) AT(ACT)
    AA(AG) GG(AGCT) GC(AGCT) AA(CT) AT(ACT)
    (CT)T      3'

SEQ ID No. 6:

5'  TCG GAA TTC (CT)TC (AGCT)GG (AGCT)GC CAT CCA
    (AG)TA     3'

SEQ ID No. 7:

5'  TCG GAA TTC (CT)TC (AGCT)GG (AGCT)GC CAT CCA
    (AG)AA     3'

Fig. 3

```
         1                                                       50
12-2    ................  ..........MQ NLKADPEELF TKLEKIGKGS FGEVFKGIDN
  5e    ......MAHS PVAVQVPGMQ NNIADPEELF TKLERIGKGS FGEVFKGIDN
 S201   METVQLRNPP RRQLKKLDED SLTKQPEEVF DVLEKLGEGS YGSVYKAIHK 51                                                     100
12-2    RTQKVVAIKI IDLEEAEDEI EDIQQEITVL SQCDSPYVTK YYGSYLKDTK
  5e    RTQQVVAIKI IDLEEAEDEI EDIQQEITVL SQCDSSYVTK YYGSYLKGSK
 S201   ETGQIVAIKQ VPV...ESDL QEIIKEISIM QQCDSPHVVK YYGSYFKNTD 101                                                     150
12-2    LWIIMEYLGG GSALDL..LE PGPLDEIQIA TILREILKGL DYLHSEKKIH
  5e    LWIIMEYLGG GSALDL..LR AGPFDEFQIA TMLKEILKGL DYLHSEKKIH
 S201   LWIVMEYCGA GSVSDIIRLR NKTLTEDEIA TILQSTLKGL EYLHFMRQIH 151                                                     200
12-2    RDIKEANVLL SEHGEVKLAD FGVAGQLTDT QIKRNTFVGT PFWMAPEVIK
  5e    RDIKAANVLL SEQGDVKLAD FGVAGQLTDT QIKRNTFVGT PFWMAPEVIQ
 S201   RDIKAGNILL NTEGHAKLAD FGVAGQLTDT MAKRNTVIGT PFWMAPEVIQ 201                                                     250
12-2    QSAYDSKADI WSLGITAIEL AKGEPPHSEL HPMKVLFLIP KNNPPTL..E
  5e    QSAYDSKADI WSLGITAIEL AKGEPPNSDM HPMRVLFLIP KNNPPTL..I
 S201   EIGYHCVADI WSLGITAIEM AEGKPPYADI HPMRAIFMIP TNPPPTFRKP 251                                                     300
12-2    GNYSKPLKEF VEACLNKEPS FRPTAKELLK HKFIIRNAKK TSYLTELID.
  5e    GDFTKSFKEF IDACLNKDPS FRPTAKELLK HKFIVKNSKK TSYLTELID.
 S201   ELWSDNFMDF VKQCLVKSPE QRATATQLLQ HPF.VKSAKG VSILRDLINE 301                                                     350
12-2    ....RYKR.. ...WKAE.QS HEDSSSEDSD VETDGQASGG SDSGDWIFTI
  5e    ....RFKR.. ...WKAEGHS DEESDSEGSD SESSSRESNP HPEWSFTTVR
 S201   AMDVKLKRQE AQQREVDQDD EENSEEDEMD SGTMVRTAGD EMGTVRVAST 351                                                     400
12-2    REKDPKNL.. .......... ......ENGT LQLSDLERNK MKDIPKKPFS
  5e    KKPDPKKL.. .......... ......QNGE EQ........ .......DLV
 S201   MSGGANTMIE HGDTLPSQLG TMVINTEDEE EEGTMKRRDE TMQPAKPSFL 401                                                     450
12-2    QCFIPQSFLL LFCGAEKTKS QGMRRELGVN RRAAGEPSTW RKRPALGSQT
  5e    QTLSCLSMII TPAFAE.... ..LKQQDENN ASPNQAIEEL EKSIAVA...
 S201   EYFEQKEKEN QINSFGKNVS GSLKNSSDWK IPQDGDYEFL KSWTVEDLQK 451                                                     496
12-2    LWWHSLCSGC RDIL...... .......... ..........
  5e    ...ETACPGI TDKMVKKLIE KFQKCSADES P......... ......
 S201   RLL......AL DPMMEQEMEE IRQKYRSKRQ PILDAIEAKK RRQQNF
```

Fig. 4

```
C12.2bs    1 MAHSPVAVQVPGMQNNIADPEELFTKLERIGKGSFGEVFKGIDNRTQQVV  50
               |||     ||||||||||||:|||||||||||||||||||·||
5e.new     1 ..........MQNLKADPEELFTKLEKIGKGSFGEVFKGIDNRTQKVV  38

C12.2bs   51 AIKIIDLEEAEDEIEDIQQEITVLSQCDSSYVTKYYGSYLKGSKLWIIME 100
             |||||||||||||||||||||||||||||·||||||||||:·|||||||
5e.new    39 AIKIIDLEEAEDEIEDIQQEITVLSQCDSPYVTKYYGSYLKDTKLWIIME  88

C12.2bs  101 YLGGGSALDLLRAGPFDEFQIATMLKETLKGLDYLHSEKKIHRDIKAANV 150
             ||||||||||| :||:||:||||:|:|:||||||||||||||||||·|||
5e.new    89 YLGGGSALDLLEPGPLDEIQIATILREILKGLDYLHSEKKIHRDIKEANV 138

C12.2bs  151 LLSEQGDVKLADFGVAGQLTDTQIKRNTFVGTPFWMAPEVIQQSAYDSKA 200
             ||||:|:||||||||||||||||||||||||||||||||||||·||||||||
5e.new   139 LLSEHGEVKLADFGVAGQLTDTQIKRNTFVGTPFWMAPEVIKQSAYDSKA 188

C12.2bs  201 DIWSLGITAIELAKGEPPNSDMHPMRVLFLIPKNNPPTLIGDFTKSFKEF 250
             ||||||||||||||||||:|::|||:||||||||||||| |::·|·:|||
5e.new   189 DIWSLGITAIELAKGEPPHSELHPMKVLFLIPKNNPPTLEGNYSKPLKEF 238

C12.2bs  251 IDACLNKDPSFRPTAKELLKHKFIVKNSKKTSYLTELIDRFKRWKAEGHS 300
             ::|||||:|||||||||||||||||::|·|||||||||||:|||||| :|
5e.new   239 VEACLNKEPSFRPTAKELLKHKFIIRNAKKTSYLTELIDRYKRWKAE.QS 287

C12.2bs  301 DEESDSEGSDSESSSRESNPHPEWSFTTVRKKPDPKKLQNGEEQ...... 344
             ·|:|·||:|| |·.::..|.. .. .:. .:..|||·|:||· |
5e.new   288 HEDSSSEDSDVETDGQASGGSDSGDWIFTIREKDPKNLENGTLQLSDLER 337

C12.2bs  345 .........DLVQTLSCLSMIITPAFAE......LKQQDENNASRNQAIE 379
                      .:|.: ·|:::  · || :::·:  : |  . ...·
5e.new   338 NKMKDIPKKPFSQCFIPQSFLLLFCGAEKTKSQGMRRELGVNRRAAGEPS 387

C12.2bs  380 ELEKSIAVA......ETACPGITDKMVKKLIEKFQKCSADESP 416
             .:  |.  |::       .. |·|· | :
5e.new   388 TWRKRPALGSQTLWWHSLCSGCRDIL................ 413
```

Fig. 5

12-2  Length: 1744

```
   1  GGCACGAGCC AGCGCTCGCG GGCCCAGGCC GCCCGGCTCG ACCTGAGCAC
  51  CGCGGCGGCG CAGCGACGGG ATCCCTGGAG AAGCAGCCGC AGTCTCGAGA
 101  CGTCCCCCGC GCCCCCACT GCCCGCCCCA GGCTCAGTGT ATGGGGCCGC
 151  GGCCCGCCAA CCTTCGTTGA GACCGTCCCC GGGGTGCGGT GGCCTCGGGC
 201  TCCAGAGCCC GCCCCGCCAC CCGAGGGCTG CGCGCGGCCC CGGGCCTGCT
 251  CGCCGCGCGG CTCCGCGCGT CCCGGGCCAG GAAGTGGCGG CGCCGAGCGC
 301  CATGGCCCAC TCCCCGGTGC AGTCGGGCCT GCCGGGCATG CAGAACCTGA
 351  AAGCAGACCC AGAAGAGCTT TTTACCAAGC TAGAGAAGAT TGGAAAGGGC
 401  TCTTTTGGTG AAGTGTTCAA AGGCATTGAC AATCGGACTC AGAAAGTGGT
 451  GGCCATAAAA ATCATTGATC TGGAAGAAGC CGAGGACGAG ATAGAGGACA
 501  TCCAACAAGA GATCACAGTG CTGAGCCAGT GTGACAGTCC CTACGTCACC
 551  AAGTACTATG GATCCTATCT CAAGGATACT AAGTTGTGGA TAATCATGGA
 601  GTATCTTGGT GGAGGCTCTG CCCTGGATCT GTTAGAGCCT GGCCCTTTAG
 651  ATGAAATTCA GATTGCAACC ATATTACGAG AAATTCTGAA AGGACTTGAT
 701  TATCTACACT CGGAGAAGAA AATTCACAGA GATATTAAAG CGGCCAATGT
 751  TCTGCTCTCT GAACATGGAG AGGTGAAGCT GGCAGACTTT GGAGTGGCCG
 801  GCCAGCTGAC GGATACCCAG ATCAAAAGGA ACACCTTCGT GGGTACCCCC
 851  TTCTGGATGG CGCCGGAGGT CATCAAGCAG TCAGCCTACG ACTCAAAGGC
 901  AGACATCTGG TCCCTTGGCA TCACCGCAAT AGAACTGGCC AAAGGAGAGC
 951  CACCACATTC TGAGCTGCAC CCCATGAAGG TGTTATTCCT CATCCCAAAG
1001  AACAACCCTC CCACACTGGA AGGGAACTAC AGCAAACCCC TCAAGGAGTT
1051  CGTGGAGGCC TGCCTGAACA AGGAGCCCAG CTTTAGGCCC ACTGCTAAGG
1101  AATTATTGAA GCACAAATTC ATAATCCGCA ATGCAAAGAA AACGTCCTAC
```

FIG. 6A

```
1151    TTGACCGAGC TTATCGACAG GTACAAGAGG TGGAAGGCGG AGCAGAGCCA
1201    CGAGGACTCC AGCTCGGAGG ACTCTGACGT GGAGACAGAT GGCCAGGCGT
1251    CTGGAGGCAG CGACTCTGGG GACTGGATCT TCACTATCCG GGAGAAAGAT
1301    CCCAAGAATC TGGAGAACGG AACTCTTCAG CTCTCGGACT TGGAAAGAAA
1351    TAAGATGAAA GATATCCCAA AGAGGCCTTT CTCTCAGTGT TTATCCACAA
1401    TCATTTCTCC TCTGTTTGCG GAGCTGAAAG AGAAGAGCCA GGCATGCGGA
1451    GGGAACTTGG GGTCAATAGA AGAGCTGCGG GGAGCCATCT ACTTGGCGGA
1501    AGAGGCCTGC CCTGGGATCT CAGACACTAT GGTGGCACAG CTTGTGCAGC
1551    GGCTGCAGAG ATATTCTCTG AGTGGCGGAG GAGCCTCAGC GCACTGAAGG
1601    CCCATGGCGC CCGGGTTGGT TTTTCCTTTC TTCTTCATCT TCCTTCTTTT
1651    TAAAAGTCAA CGAGAGCCTT TGCCGACTCT GCGAAGAGGT GTCACGGAGG
1701    GGCCCACCCG CCCTCCCATA GCGCCGGCAC CTGTCCCTCG TGCC
```

FIG. 6B

```
              1                                                    50
 Pep12-2   ....MAHSPV QSGLPGMQN. .LKADPEELF TKLEKIGKGS FGEVFKGIDN
   Pep5e   ....MAHSPV AVQVPGMQN. .NIADPEELF TKLERIGKGS FGEVFKGIDN
 Peps201   METVQLRNPP RRQLKKLDED SLTKQPEEVF DVLEKLGEGS YGSVYKAIHK 51                                                  100
 Pep12-2   RTQKVVAIKI IDLEEAEDEI EDIQQEITVL SQCDSPYVTK YYGSYLKDTK
   Pep5e   RTQQVVAIKI IDLEEAEDEI EDIQQEITVL SQCDSSYVTK YYGSYLKGSK
 Peps201   ETGQIVAIKQ VPV...ESDL QEIIKEISIM QQCDSPHVVK YYGSYFKNTD 101                                                 150
 Pep12-2   LWIIMEYLGG GSALDL..LE PGPLDEIQIA TILREILKGL DYLHSEKKIH
   Pep5e   LWIIMEYLGG GSALDL..LR AGPFDEFQIA TMLKEILKGL DYLHSEKKIH
 Peps201   LWIVMEYCGA GSVSDIIRLR NKTLTEDEIA TILQSTLKGL EYLHFMRQIH 151                                                 200
 Pep12-2   RDIKAANVLL SEHGEVKLAD FGVAGQLTDT QIKRNTFVGT PFWMAPEVIK
   Pep5e   RDIKAANVLL SEQGDVKLAD FGVAGQLTDT QIKRNTFVGT PFWMAPEVIQ
 Peps201   RDIKAGNILL NTEGHAKLAD FGVAGQLTDT MAKRNTVIGT PFWMAPEVIQ 201                                                 250
 Pep12-2   QSAYDSKADI WSLGITAIEL AKGEPPHSEL HPMKVLFLIP KNNPPTL..E
   Pep5e   QSAYDSKADI WSLGITAIEL AKGEPPNSDM HPMRVLFLIP KNNPPTL..I
 Peps201   EIGYHCVADI WSLGITAIEM AEGKPPYADI HPMRAIFMIP TNPPPTFRKP 251                                                 300
 Pep12-2   GNYSKPLKEF VEACLNKEPS FRPTAKELLK HKFIIRNAKK TSYLTELID.
   Pep5e   GDFTKSFKEF IDACLNKDPS FRPTAKELLK HKFIVKNSKK TSYLTELID.
 Peps201   ELWSDNFMDF VKQCLVKSPE QRATATQLLQ HPF.VKSAKG VSILRDLINE 301                                                 350
 Pep12-2   ....RYKRWK A...E.QSHE DSSSEDSDVE TDGQASGGSD SGDWI.....
   Pep5e   ....RFKRWK A...EGHSDE ESDSEGSDSE SSSRESNPHP EWSFT.....
 Peps201   AMDVKLKRQE AQQREVDQDD EENSEEDEMD SGTMVRTAGD EMGTVRVAST 351                                                 400
 Pep12-2   ......FTIR EKDPKNLENG TLQLSDLERN KMKDIPKRPF SQCLSTIISP
   Pep5e   ......TVRK KPDPKKLQNG E......EQD LVQTLS.... ..CLSMIITP
 Peps201   MSGGANTMIE HGDTLPSQLG TMVINTEDEE EEGTMKRRDE TMQPAKPSFL 401                                                 450
 Pep12-2   LFAELKEKSQ ACGGNLGSIE ELRGAIYLAE EACPGISDTM VAQLVQRLQR
   Pep5e   AFAELKQQDE NNASRNQAIE ELEKSIAVAE TACPGITDKM VKKLIEKFQK
 Peps201   EYFEQKEKEN QINSFGKNVS GSLKNSSDWK IPQDGDYEFL KSWTVEDLQK 451                                491
 Pep12-2   YSLSGGGASA H.......... ..........  ...........
   Pep5e   CSADESP... ..........  ..........  ...........
 Peps201   RLLALDPMME QEMEEIRQKY RSKRQPILDA IEAKKRRQQN F
```

FIG. 7

Pep12-2 x Pep5e

```
  1 MAHSPVQSGLPGMQNLKADPEELFTKLEKIGKGSFGEVFKGIDNRTQKVV  50
    ||||||.  .:|||||   |||||||||||:|||||||||||||||||.||
  1 MAHSPVAVQVPGMQNNIADPEELFTKLERIGKGSFGEVFKGIDNRTQQVV  50

51 AIKIIDLEEAEDEIEDIQQEITVLSQCDSPYVTKYYGSYLKDTKLWIIME 100
    |||||||||||||||||||||||||||||.||||||||||||:.|||||||
 51 AIKIIDLEEAEDEIEDIQQEITVLSQCDSSYVTKYYGSYLKGSKLWIIME 100

101 YLGGGSALDLLEPGPLDEIQIATILREILKGLDYLHSEKKIHRDIKAANV 150
    ||||||||||| :||:||:||||:|:||||||||||||||||||||||||
101 YLGGGSALDLLRAGPFDEFQIATMLKEILKGLDYLHSEKKIHRDIKAANV 150

151 LLSEHGEVKLADFGVAGQLTDTQIKRNTFVGTPFWMAPEVIKQSAYDSKA 200
    ||||:|:|||||||||||||||||||||||||||||||||||.|||||||
151 LLSEQGDVKLADFGVAGQLTDTQIKRNTFVGTPFWMAPEVIQQSAYDSKA 200

201 DIWSLGITAIELAKGEPPHSELHPMKVLFLIPKNNPPTLEGNYSKPLKEF 250
    |||||||||||||||||:|::|||:||||||||||||||| |::.|.:|||
201 DIWSLGITAIELAKGEPPNSDMHPMRVLFLIPKNNPPTLIGDFTKSFKEF 250

251 VEACLNKEPSFRPTAKELLKHKFIIRNAKKTSYLTELIDRYKRWKAE.QS 299
    ::||||| :||||||||||||||||::|.||||||||||||:||||||  :|
251 IDACLNKDPSFRPTAKELLKHKFIVKNSKKTSYLTELIDRFKRWKAEGHS 300

300 HEDSSSEDSDVETDGQASGGSDSGDWIFTIREKDPKNLENGTLQLSDLER 349
    .|:|.||:||  |..:..|..  ..  .:.  .:..|||.|:||.     |.
301 DEESDSEGSDSESSSRESNPHPEWSFTTVRKKPDPKKLQNGE......EQ 344

350 NKMKDIPKRPFSQCLSTIISPLFAELKEKSQACGGNLGSIEELRGAIYLA 399
    :  :..:.      ||| ||.| |||||:..:.  :::  ..||||  .| :|
345 DLVQTLS......CLSMIITPAFAELKQQDENNASRNQAIEELEKSIAVA 388

400 EEACPGISDTMVAQLVQRLQRYSLSGGGASAH 431
    |.||||||.|.||  .|:::|::|  .::.
389 ETACPGITDKMVKKLIEKFQKCSADESP.... 416
```

FIG. 8

TWO STERILE-20 KINASE-LIKE PROTEINS AND METHODS OF USE THEREOF

RELATED APPLICATION

This application is a Continuation-in-Part of U.S. application Ser. No. 09/591,083, filed Jun. 9, 2000 pending, which is a Continuation of PCT/US98/26116, filed Dec. 9, 1998, which claims benefit of U.S. Provisional application 60/069,078, filed Dec. 9, 1997 now abandoned the entire teachings of which are incorporated herein by reference.

GOVERNMENT SUPPORT

This invention was supported in whole or in part, by 2polh132262-15 from the National Institutes of Health. The Government has certain rights in the invention.

BACKGROUND

Protein kinases play a key role in cell growth and differentiation. The p21-activated proteins kinases (PAKs) are related to a yeast serine/threonine protein kinase, Ste20. Ste20 is a member of a growing family of regulatory enzymes that may play roles in diverse phenomena such as cellular morphogenesis, the stress response and the pathogenesis of AIDS.

The growth, differentiation, maintenance and senescence of cells requires the transmission of signals. These signals can be derived from extracellular stimuli, such as hormone interaction with its receptor or physiological stress, or may be derived intracellularly from developmental programs.

The signals are transmitted via a signal cascade wherein proteins are phosphorylated or dephosphorylated in sequence. Protein kinases, the enzymes that phosphorylate, play a key role in many signaling pathways and therefore protein kinases play a key role in cell growth and differentiation. Protein kinases fall into two broad categories, tyrosine kinases (those that add phosphate to tyrosine residues) and serine/threonine kinases (those that add phosphate to either serine or threonine residues).

One group of signaling pathways involving protein kinases are the mitogen-activated protein (MAP) kinase cascades. The MAP kinase cascades are now recognized to participate in diverse signal transduction pathways rather than only mediating mitogenic signals from all surface receptors (Davis, R. J., 1994, *Trends in Biochem Science*, 19:470–473).

Genetic analyses in yeast have made it possible to identify some of the components of MAPK pathways, and to clarify the diversity of their functions and regulation (Herskowitz, I., 1995, *Cell* 80:187–197). Mammalian cells have at least three MAPK pathway subtypes, the ERK (extracellular signal-regulated protein kinase) pathway, JNK (c-Jun NH$_2$-terminal kinase)/SAPK (stress-activated protein kinase) pathway, and P38/Mpk2 pathway; together, these pathways mediate a wide variety of physiological responses (Davis, R. J., 1994, *Trends in Biochem. Science* 19:470–473; Derijard, B. et al., 1994 *Cell* 76:1025–1037; Kyriakis, J. M. et al., 1994 *Nature* 369:156–160; Han, J. et al., 1994 *Genes Dev.* 3:1336–1348; Lee, J. C. et al., 1994 *Nature* 372:739–746; Rouse, J. et al., 1994 *Cell* 78:1027–1037). MAPKs are activated by sequential protein phosphorylation reactions. The basic framework of the MAP kinase pathway, where MAPK is phosphorylated on Thr and Tyr residues and activated by MAPK kinase (MAPKK), before which MAPKK is itself phosphorylated and activated by MAPKK kinase (MAPKKK), is common from yeast to mammals (Nishida, E. and Gotoh, Y., 1993 *Trends in Biochem. Science* 18:128–131; Davis, 1994; Herskowitz, 1995; Marshall, C. J., 1994 *Curr. Opin. Genet. Dev.* 4:82–89).

A new kinase group activated by G-protein and thought to act as MAPKKK kinase (MAPKKKK) has been identified in both yeast and mammals. In budding yeast, this new kinase group is known by its prototype member Sterile 20 (Ste20). Ste20 is activated by the βα complex released from the heterotrimeric G protein complex upon pheromone receptor stimulation, and in turn activates Ste11 (a MAPKKK) (Leberer, E. et al., 1992 *EMBO J*. 11:4815–4824; Ramer, S. W. and Davis, R. W., 1993 *Proc. Natl. Acad. Sci. U.S.A*. 90:452–456). In mammals, this new kinase group is known by its prototype member p21-activated protein kinase (PAK). PAK (now called α-PAK) has been identified as a protein kinase activated by the Rho family of small G-proteins, Rac1 and Cdc42 (Manser, E. et al., 1994 *Nature* 367:40–46); PAK also shows sequence similarity to yeast Ste20. Recently it has been clarified that PAK comprises a protein kinase family composed of several PAK isoforms, hPAK65 (Martin, G. A. et al., 1995 *EMBO J*. 14:1970–1978), MPAK-3 (Bagrodia, S. et al., 1995 *J. Biol. Chem*. 270:22731–22737 and β-PAK (Manser, E. et al., 1995 *J. Biol. Chem*. 270:25070–25078), all of which are able to interact with Cdc42 and Rac1. Rac1 and Cdc42 have been implicated not only in cell motility (Ridley, A. J. et al., 1992 *Cell* 70:401–410; Kozma, R. et al., 1995 *Mol. Cell. Biol*. 15:1842–1952; Nobes, C. D. and Hall, A., 1995 *Cell* 81:53–62), but also in the preferential activation of the JNK/SAPK and p38/Mpk2 pathways rather than the ERK pathway (Coso, O. A. et al., 1995 *Cell* 81:1137–1146; Minden, A. et al., 1995 *Cell* 81:1147–1157; Olson, M. F. et al., 1995 *Science* 269:1270–1272). This is in contrast to another small G-protein, Ras, which predominantly activates the ERK pathway through Raf activation (Minden, A. et al., 1994 *Science* 266:1719–1723). Although a direct interaction between PAKs and components of the JNK/SAPK and p38/Mpk2 pathways has not yet been demonstrated, these observations raise the intriguing possibility that PAK or PAK-related proteins mediate the signals from Rac1 and Cdc42 to the JNK/SAPK and p38/Mpk2 pathways, and, furthermore, that G-proteins differentially regulate MAPK pathways to achieve various physiological responses.

In contrast to the above-mentioned kinases, a group of Ste20-related kinases that lack the putative Cdc42/Rac1-binding domain has been identified in both yeast and mammals: Sps1, an upstream regulator of the MAPK pathways (Freisen et al., *Genes and Dev*., 9:2162–2175 (1994) and MST-1 in Mammals; Creasy, C. L. and Chernoff, J., 1995 *J. Biol. Chem*. 270:21695–21700). Although the specific activation of the SAPK pathway by GCK has recently been reported (Pombo, C. M. et al., 1995 *Nature* 377:750754), the upstream and downstream signaling pathways of this group of kinases remain to be clarified. Sterile 20-related kinases are regulatory molecules involved in mitogenic signaling as well as other cellular phenomena such as morphology and motility. These phenomena are important factors in development, cell differentiation, cancer and metastases. Therefore, the polynucleotides and polypeptides of the present invention allow manipulation of the signaling pathways involved and will allow the development of reagents to modulate the signaling pathways involved in these important cellular phenomena.

SUMMARY OF THE INVENTION

The present invention relates to isolated polynucleotides encoding novel members of the Ste20 family of serine/ threonine protein kinases, and the recombinantly produced polypeptides encoded by said polynucleotides.

The present invention is drawn to a purified nucleic acid comprising at least 45 continuous nucleotides of a nucleic acid sequence provided in SEQ ID NO: 3. The purified nucleic acid can comprise SEQ ID NO: 3, a complementary sequence or a sequence having greater about 600 bases in length, wherein said sequence hybridizes to SEQ ID NO: 3 under stringent conditions.

The present invention is also drawn to a purified nucleic acid selected from the group consisting of: SEQ ID NO: 1, SEQ:ID NO: 9, a sequence complementary to either SEQ ID NO: 1 or 9 and a sequence greater than 500 bases in length wherein said sequence hybridizes to SEQ ID NO: 1 or 9 under stringent conditions.

The present invention also encompasses expression vectors comprising the polynucleotides of the present invention and host cells harboring said vectors.

The present invention is also drawn to a purified nucleic acids encoding an amino acid sequence comprising SEQ ID NOs.: 2, 4, or 10. In one embodiment, the purified nucleic acid sequence comprising a nucleic acid sequence encoding at least 100 continuous amino acids of an amino acid sequence provided in SEQ ID NO: 2 or SEQ ID NO: 10. In another embodiment, the purified nucleic acid sequence comprising a nucleic acid sequence encoding at least 54 continuous amino acids of an amino acid sequence provided in SEQ ID NO: 4. The method of the present invention is also drawn to a method of making polypeptides encoded by SEQ ID NOs.:1, 3, or 9 comprising, transfecting a host cell with an expression vector comprising SEQ ID NOs.: 1, 3, or 9 and isolating the expressed protein.

The present invention is further drawn to polypeptides comprising SEQ ID NOs.: 2 or 10 and biologically active fragments thereof, polypeptides functionally equivalent to polypeptides comprising SEQ ID NOs.: 2 or 10 or fragments thereof, antibodies that bind to polypeptides encoded by SEQ ID NOs.:1, 3, or 9.

The present invention is further drawn to a serine/threonine kinase comprising the amino acid sequence of SEQ ID NOs. 2, 4, or 10.

The protein kinases described herein have homology with a family of proteins that appear to function in the mitogen-activated protein (MAP) kinase cascade. The present invention also relates to methods of using the polynucleotides and polypeptides described herein to detect, isolate and characterize elements upstream and downstream of the novel kinase in the signal transduction pathway using assays well known in the art such as kinase assays or co-immunoprecipitation assays, or combinations thereof. Furthermore, polypeptides of the present invention include biologically active fragments of the proteins described herein. Such proteins and biologically active fragments are useful to generate antibodies that specifically bind the proteins of the present invention. The biologically active fragments are also useful as tools to study the activity of the protein. Altered forms of the polypeptides are within the scope of the present invention and can be used to study the activity of downstream elements in the signaling pathway or to generate specific antibodies.

The isolated polynucleotides and polypeptides of the present invention provide the advantage of being able to conveniently manipulate the genes, gene products and expression level of the gene product, to facilitate understanding of how Ste20 and Ste20 family members regulate signal transduction in the cell.

BRIEF DESCRIPTION OF THE DRAWINGS

FIG. 1 depicts a C12-2bs cDNA sequence (SEQ ID NO. 1).

FIGS. 2A and 2B depicts the cDNA sequence encoding 5e.new (SEQ ID NO. 3).

FIG. 3 depicts the PCR primers (SEQ ID NOs. 5–7) used to clone the novel genes of the present invention.

FIG. 4 depicts an alignment of amino acid sequences of C12-2bs, SEQ ID NO. 2 (as encoded by SEQ ID NO. 1), 5e.new (SEQ ID NO. 4) and S201 (SEQ ID NO. 8), mouse Ste20 homologue.

FIG. 5 depicts an amino acid sequence alignment between C12-2bs SEQ ID NO. 2 (as encoded by SEQ ID NO. 1) and 5e.new (SEQ ID NO. 4).

FIGS. 6A and 6B depicts C12-2bs cDNA (SEQ ID NO. 9) having additional 5' sequence and having a frame shift correction near the 3' terminus.

FIG. 7 depicts an alignment of amino acid sequences of C12-2bs, SEQ ID NO. 10 (encoded by SEQ ID NO. 9), 5e.new (SEQ ID NO. 4) and S201 (SEQ ID NO. 8), mouse Ste20 homologue.

FIG. 8 depicts an amino acid sequences alignment between C12-2bs, SEQ ID NO. 10 (encoded by SEQ ID NO. 9) and 5e. new (SEQ ID NO. 4).

DETAILED DESCRIPTION OF THE INVENTION

Ste20/PAK serine/threonine protein kinases (referred to herein as Sterile 20 protein kinases or Ste20) have been suggested as playing essential roles in diverse phenomena such as cellular morphogenesis, the stress response and the pathogenesis of AIDS. Recently, mammalian Ste20 family members have been discovered that do not appear to participate in the three known MAP kinase cascades. While much is known about the Ste20 family of protein kinases and their interaction with the MAP kinase cascade, it is clear that the full extent of the Ste20 family as well as the upstream and downstream regulatory components are poorly understood.

Described herein are new members of the Ste20 family that were cloned from a murine cDNA library using polymerase chain reaction (PCR). Degenerate primers SEQ ID NO. 5, SEQ ID NO. 6 and SEQ ID NO. 7 (FIG. 3) were used in the following combinations: SEQ ID NO. 5 with SEQ ID NO. 6, and SEQ NO. 5 with SEQ ID NO. 7, in a standard PCR reaction as described in the Exemplification. Novel members of the Ste20 family were isolated and are shown in FIGS. 1, 2 and 6 (SEQ ID NOs. 1, 3 and 9, respectively), where SEQ ID NO. 9 has additional 5' sequence and a frame shift correction compared to SEQ ID NO. 1.

The present invention encompasses the isolated and/or recombinant nucleic acid sequences encoding novel members of the Sterile 20 family of serine/threonine protein kinases, functional equivalents thereof or biologically active fragments thereof, as described herein. The present invention further encompasses sequences complementary to, or homologous with SEQ ID NOs. 1, 3 and 9.

The polynucleotides of the present invention, or portions thereof, can be used as probes to isolate and/or clone substantially similar or functionally equivalent homologues of the Ste20 family of proteins. The polynucleotides of the present invention can also be used as probes to detect and or measure expression of the genes encoded by the present invention. Expression assays, such as Southern blot analysis and whole mount in situ hybridization are Well known in the art. The polynucleotides of the present invention, or portions thereof, can be used as primers to clone homologues or family members by PCR using techniques well known in the art.

As used herein, nucleic acids are also referred to as DNA and RNA, or DNA sequences and RNA sequences, or DNA molecules or RNA molecules. Nucleic acids referred to herein as "isolated" or "purified" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods known to those of skill in the art to obtain isolated nucleic acids and methods described herein. These isolated nucleic acids include essentially pure nucleic acids, nucleic acids produced by chemical synthesis, by combinations of biological and chemical methods, and recombinant nucleic acids produced by recombinant methods, which are well known in the art.

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Also encompassed by the present invention are nucleic acid sequences (DNA or RNA sequences) which are complementary, substantially homologous to, or functionally equivalent to the Sterile 20 protein kinase DNA sequences described herein. Fragments of the sequences, complementary sequences, substantially homologous sequences and functionally equivalent sequences are also encompassed by the present invention. Nucleic acid sequences hybridizing with sequences comprising SEQ ID NOs 1, 3 and 9 and portions thereof under conditions of stringency known to those of skill in the art to be sufficient to identify DNA sequences with substantial nucleic acid sequence identity are also encompassed by the present invention. Due to the degeneracy of the genetic code, different combinations of nucleotides can encode for the same polypeptide or the homologous polypeptide in a different organism. Thus, different nucleic acids can encode the same Sterile 20 protein or Sterile 20 homologue. These polynucleotides are referred to herein as functionally equivalent polynucleotides. In preferred embodiments, substantially homologous polynucleotides of the present invention comprise at least 10, at least 27, at least 45, at least 102, at least about 500 or at least about 600 continuous nucleotides of SEQ ID NOs.: 1, 3 or 9. It is reasonable to predict that DNA sequences identified under such stringent conditions will likely encode a protein (also referenced to herein as a polypeptide, or peptide fragment) with the biological activity or physical characteristics of Sterile 20 protein kinases comprising SEQ ID NOs 2, 4 or 10. The nucleic acid of the present invention preferably encodes 8, 18, 34, 54 or 100 continuous amino acids of the amino acid sequences provided in SEQ ID NO. 2, 4 or: 10.

Polypeptides with the biological activity or physical characteristics of Sterile 20 protein kinases comprising SEQ ID NOs 2, 4 or 10 are referred to herein as functionally equivalent polypeptides. "Functional or biologically active protein" is defined herein as a protein which shares significant identity (e.g., at least about 65%, preferably at least about 80% and most preferably at least about 95%) with the corresponding sequences of the endogenous protein and possesses one or more of the functions thereof.

"Polypeptide" as used herein indicates a molecular chain of amino acids and does not refer to a specific length of the product. Thus, peptides, polypeptides and proteins are included within the definition of polypeptide. This term is also intended to refer to post-expression modifications of the polypeptide, for example, glycosylations, acetylations, phosphorylations and the like.

A general description of stringent hybridization conditions are discussed in Ausubel, F. M., et al., *Current Protocols in. Molecular Biology*, Greene Publishing Assoc. and Wiley-Interscience 1989, the teachings of which are incorporated herein by reference. Factors such as probe length, base composition, percent mismatch between the hybridizing sequences, temperature and ionic strength influence the stability of nucleic acid hybrids. Thus, stringency conditions sufficient to identify the polynucleotides of the present invention, (e.g., high or moderate stringency conditions) can be determined empirically, depending in part upon the characteristics of the known DNA to which other unknown nucleic acids are being compared for sequence similarity.

Alternatively, conditions for stringency are as described in WO 98/40404, the teachings of which are incorporated herein by reference. In particular, examples of highly stringent, stringent, reduced and least stringent conditions are provided in WO 98/40404 in the Table on page 36. In one embodiment, highly stringent conditions are those that are at least as stringent as, for example, 1×SSC at 65° C., or 1×SSC and 50% formamide at 42° C. Moderate stringency conditions are those that are at least as stringent as 4×SSC at 65° C., or 4×SSC and 50% formamide at 42° C. Reduced stringency conditions are those that are at least as stringent as 4×SSC at 50° C., or 6×SSC and 50% formamide at 40° C.

As defined herein, substantially complementary means that the sequence need not reflect the exact sequence of e.g., SEQ ID:NOs. 1, 3 or 9, but must be sufficiently similar in identity of sequence to hybridize with SEQ ID NOs. 1, 3 or 9 under stringent conditions. For example, non-complementary bases, or longer or shorter sequences can be interspersed in sequences, provided the sequence has sufficient complementary bases with, e.g., SEQ ID NOs. 1, 3 or 9 to hybridize therewith. Under stringent hybridization conditions, only highly complementary nucleic acid sequences hybridize. Preferably, such conditions prevent hybridization of nucleic acids having four mismatches out of 20 continuous nucleotides, more preferably two mismatches out of 20 continuous nucleotides, most preferably one mismatch out of 20 continuous nucleotides.

Biological functions of the Sterile 20 kinase proteins include phosphorylation of serine and threonine residues in response to extracelluary derived or intracellularly derived stimuli. Phosphorylation activity can be measured using methods well know in the art. For example, the kinase of the present invention can be epitope-tagged using methods well known in the art. The tagged protein are then expressed in suitable cells, such as COS7 cells, using methods well known in the art. The cells are then stimulated or not, to activated the Sterile 20 signal transduction pathway and lysed under appropriate conditions. The kinase is isolated by immunoprecipitation. The kinase activity is measured in a standard kinase as say with a suitable substrate, such as myelin basic protein (see, for example, Creasy and Chernoff, *J. Biol. Chem.* 270:21695–21700 (1995)). The present invention also pertains to an isolated nucleic acid sequence encoding an altered kinase protein, wherein the kinase has altered activity. The activity can be enhanced or reduced or abolished. The alteration can result in a constitutively active kinase. In one embodiment, the resulting alteration in amino acid sequence is in the catalytic domain of the kinase.

Biological activity of the present invention further includes the ability to bind the normal upstream (for example an activator). or downstream (for example the target to be phosphorylated) element in the signaling pathway. Also described herein, biological activity can include the antigenicity of the protein, or peptide, resulting in the production of antibodies which bind to the polypeptides, Sterile 20 kinases and serine/threonine kinases of the present invention.

The present invention also relates to methods of altering the biological activity of the polypeptides of the present invention. Alteration can be, for example, an increase or decrease in serine/threonine kinase activity, alteration in cellular localization of the protein or alteration in interaction of the polypeptides of the present invention with upstream or downstream elements of the signaling pathway.

The present invention is understood to include the polypeptides having amino acid sequences comprising SEQ ID NOs. 2 , 4 or 10. The present invention includes polypeptides comprising amino acid sequences analogous to SEQ ID NOs. 2 , 4 or 10. Such proteins are defined herein as C12-2bs or 5e.new analogs, or C12-2bs or 5e.new variants. Analogous amino acid sequences are defined herein to mean amino acid sequences with sufficient identity of amino acid sequence with, e.g., C12-2bs or 5e.new proteins, to possess the biological activity of Sterile 20 protein kinase. The biological activity of Sterile 20 protein kinase can include, for example, the capability to phosphorylate the same target as that phosphorylated by 5e.new or C12-2bs such as serine and threonine residues of target proteins in human and animal cells in response to extracelluarly derived or intracellularly derived stimuli. For example, an analog polypeptide can be produced with "silent" changes in the amino acid sequence wherein one, or more amino acid residue differs from the amino acid residues of C12-2bs or 5e.new, yet still possess the biological activity of 5e.new or C12-2bs. Examples of such differences include additions, deletions or substitutions of residues to e.g., SEQ ID NOs. 2, 4 or 10. Also encompassed by the present invention are variant proteins that exhibit lesser or greater biological activity of the Sterile 20 protein kinases of the present invention.

Variant proteins of the present invention can be produced using in vitro and in vivo techniques well-known to those of skill in the art, for example, site-specific mutagenesis and oligonucleotide mutagenesis. Manipulations of the protein sequences can be made a the protein level as well. Any numerous chemical modifications can be carried out by known techniques including, but not limited to, specific chemical cleavage by cyanogen bromide, trypsin and papain. The proteins of the present invention can also be structurally modified or denatured, for example, by heat. In general, mutations can be conservative or non-conservative amino acid substitutions, amino acid insertions or amino acid deletions.

For example, DNA encoding a variant protein of the present invention is prepared by site-directed mutagenesis of the polynucleotides comprising SEQ ID NOs. 1, 3 or 9. Site-directed (site-specific) mutagenesis allows the production of protein variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. The term "primer" denotes a specific oligonucleotide sequence complementary to a target nucleotide sequence and used to hybridize to the target nucleotide sequence and serve as an initiation point for nucleotide polymerization catalyzed by either DNA polymerase, RNA polymerase or reverse transcriptase. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as Edelman et al., DNA 2:183, 1983. The site-specific mutagenesis technique typically employs a phage vector that exists in both a single-stranded and double-stranded form., Typical vectors useful in site-directed mutagenesis include vectors such as the M13 phage, for example, as disclosed by Messing et al., *Third Cleveland Symposium on Macromolecules and Recombinant* DNA, A. Walton, ed., Elsevier, Amsterdam, 1981. This and other phage vectors are commercially available and their use is well-known to those skilled in the art. A versatile and efficient procedure for the construction of oligonucleotide directed site-specific mutations in DNA fragments using M13-derived vectors was published by Zoller, M. J. and Smith, M., *Nucleic Acids Res.* 10:6487–6500, 1982. Also, plasmid vectors that contain a single-stranded phage origin of replication can be employed to obtain single-stranded DNA, Veira et al., *Meth Enzymol.* 153:3 1987. Alternatively, nucleotide substitutions can be introduced by synthesizing the appropriate DNA fragment in vitro, and amplifying it by PCR procedures known in the art.

In general, site-specific mutagenesis herewith can be performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc Natl Acad Sci USA.* 75:5765, 1978. This primer can then be annealed with the single-stranded protein sequence-containing vector, and subjected to DNA polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector can then be used to transform appropriate host cells such as JM 101 cells, and clones can be selected that include recombinant vectors bearing the mutated sequence arrangement. Thereafter, the mutated region can be removed and placed in an appropriate expression vector for protein production.

The PCR technique can also be used in creating amino acid sequence variants of the proteins of the present invention. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers can be designed to overlap the position of the mutation and to contain the mutation; the sequence of the other primer is preferably identical to a stretch of sequence of the opposite strand of the plasmid, but this sequence can be located anywhere along the plasmid DNA. It is preferred, however, that the sequence of the second primer is located within 500 nucleotides from that of the first, such that in the end the entire amplified region of DNA bounded by the primers can be easily sequenced. PCR amplification using a primer pair like the one just described results in a population of DNA fragments that differ at the end position of the mutation specified by the primer.

The DNA fragments produced bearing the desired mutation can be used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

Another method for preparing variants, cassette mutagenesis, is based on the technique described by Wells et al. *Gene* 34, 315, 1985. The starting material can be the plasmid (or vector) comprising SEQ ID NOs. 1, 3 or 9 or a portion thereof to be mutated. The codon(s) within the polynucleotide to be mutated are identified. There must be unique restriction endonuclease sites on each side of the identified mutation site(s). If such restriction sites do not exist, they can be generated using the above-described oligonucleotide-mediated mutagenesis method to introduce them at appropriate locations in the polynucleotide. After the restriction sites have been introduced into the plasmid, the plasmid is cut at these sites to linearize it. A double stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. The plasmid now contains the mutated DNA sequence, that can be expressed to produce altered proteins with altered kinase, binding or antigenic activity.

The present invention also encompasses biologically active protein, or biologically active fragments thereof as described herein. Such fragments can include part of the full-length amino acid sequence of a Sterile 20 protein kinase yet possess biological activity. Such fragments can be produced by amino- and carboxyl-terminal deletions, as well as internal deletions. Such peptide fragments can be tested for biological activity as described herein. Thus, a functional or biologically active protein includes mutants or variants of the endogenous protein wherein one or more amino acids have been substituted, deleted or added. The biologically active fragments can be altered to have enhanced or reduced biological activity.

The biologically active fragments of the protein and polypeptides of the present invention comprise at least six continuous amino acids provided in SEQ ID. NOs.: 2, 4 or 10. The proteins and polypeptide fragments can be used, for example, for structure determination, to assay other molecules' effects on the activity of the polypeptides of the present invention. These effects can be to inhibit or enhance the biological activity or to alter the subcellular location of the protein. The proteins and polypeptide fragments of the present invention can further be used to obtain antibodies that specifically bind to the polypeptide of the present invention. A useful fragment of the polypeptide of interest comprises about 5 to about 35 amino acids of the polypeptides of the present invention.

The DNA sequences of the present invention can also be used in a recombinant construct for the infection, transfection or transformation of a cell in vitro or in vivo under control of an appropriate promoter for the expression of functional Sterile 20 protein kinases, as defined herein, in an appropriate host cell. Such recombinant constructs are also referred to herein as expression vectors. For example, a DNA sequence can be functionally ligated to a suitable promoter (e.g., a constitutive or inducible promoter or the endogenous promoter) introduced into a suitable expression vector which is then introduced into a suitable host cell. Examples of useful promoter sequences include, for example, the early and late promoters of SV40 or adenovirus, the T3 and T7 promoters, the major operator and promoter regions of phage lambda, and the like. Constitutive and inducible promoter sequences known to control the expression of genes in prokaryotic or eukaryotic cells their viruses or various combinations thereof are useful in the expression of the DNA sequences of the present invention. Suitable host cells for use in expressing the DNA sequences of the present invention include well known eukaryotic and prokaryotic hosts, such as strains of *E. coli*, Pseudomonas, Bacillus, Streptomyces, insect cells such as *Spodoptera frugiperda* (SF9), animal cells such as CHO and mouse cells, African green monkey cells such as COS1 and COS7 and human cells as well as plant cells in tissue culture. One of skill in the art may make a selection among the vectors expression control sequences and host cells without undue experimentation and without departing from the scope of this invention. The construct can also include DNA encoding one or more selectable markers (such as neo, gdhfr and hyg) or DNA encoding one or more different antigens or therapeutic proteins.

The invention also provides vectors containing the serine/threonine kinases of the present invention and altered forms thereof. Suitable vectors for use in eukaryotic and prokaryotic cells are well known in the art and are, generally commercially available, or readily prepared by the skilled artisan. For example, suitable plasmids for use include pGEX 2T/3X/4T or pET series vectors. Additional vectors can also be found in, for example, Ausubet et al., "*Current Protocols in Molecular Biology*", John Wiley & Sons, (1998) and Sambrook et al., "*Molecular Cloning: A Laboratory Manual*", 2nd Ed. (1989), the teachings of which are incorporated herein by reference.

The construct can be introduced by any suitable means, as set forth above, such as by calcium phosphate precipitation, microinjection, electroporation or infection (such as with an infectious retroviral, herpes vaccinia or adenovirus vector). The host cell can be a eucaryotic or procaryotic cell. Suitable cells include bacterial (e.g. *E. coli*) or mammalian cells. Mammalian cells include primary somatic cells, such as, epithelial cells, fibroblasts, keratinocytes, macrophages or T cells, or immortalized cell lines, such as HeLa or HT1080. The recombinant host cell can then be cultured and, optionally, selected, in vitro under appropriate conditions resulting in the expression of the protein. Alternatively, the cell can be transplanted or injected into an animal, such as a human, for in vivo expression.

The polypeptides and biologically active fragments thereof of the present invention may be isolated or purified from recombinant cells or tissue expressing said polypeptides and purified using any of a variety of conventional methods. These methods may include, for example, precipitation, such as ammonium sulfate, ethanol, acetone or immuno-precipitation, get electrophoresis, chromatographic techniques, such as normal or reversed phase liquid chromatography, HPLC, FPLC, affinity chromatography and size exclusion chromatography or a combination thereof. "Isolated or purified polypeptide" means a polypeptide of interest or fragment thereof which is essentially free, that is, contains less than about 50%, preferably less than about 70%, and more preferably, less than about 90% of cellular components with which the polypeptide of interest is naturally associated. Methods for purifying are known in the art. One of skill in the art may select the most appropriate isolation and purification technique without departing from the scope of this invention.

The present invention further relates to fusion proteins comprising the Sterile 20 protein kinases described herein (referred to herein as a first moiety) linked to a second moiety not occurring in the Sterile 20 protein kinase as found in nature. Thus, the second moiety can be a single amino acid, peptide or polypeptide. The first moiety can be in a biologically active fragment of the. polypeptide of the present invention linked at an N-terminal location, a C-terminal location or to the second moiety. The biologically active fragment of the polypeptide of the present invention can be fused at both termini to a second moiety. In one embodiment, the fusion protein comprises a Sterile 20 protein kinase protein and either a maltose binding protein (MBP) or glutathione-S-transferase (GST). In another embodiment, the second moiety is an epitope tag, such as a myc tag or an HA tag. Such fusion proteins or epitope-tagged proteins can be isolated using methods well known in the art and are useful to produce specific antibodies or can be used in vitro kinase assays.

Specific antibodies can be used to detect the presence of the polypeptides of the present invention, fragments thereof or altered forms thereof using standard enzyme-linked immunosorbant assay, radioimmunoassay and immunoblot analysis. Specific antibodies of the present invention can also be used for immuno-cytochemistry on cells or tissues. For example, polyclonal and monoclonal antibodies, including non-human and human antibodies, humanized antibodies, chimeric antibodies and antigen-binding fragments thereof (*Current Protocols in Immunology*, John Wiley & Sons, N.Y. (1994); EP Application 173,494 (Morrison); International Patent Application WO86/01533 (Neuberger); and U.S. Pat. No. 5,225,539 (Winters)), which bind to the described polypeptide or altered polypeptides or fragments thereof, are within the scope of the invention.

Antibodies of the present invention can be generated, for example, by immunizing a mammal, such as a mouse, rat, hamster or rabbit, with an immunogenic form of the polypeptides of the present invention or altered form thereof that are capable of eliciting an antibody response). Techniques for conferring immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody. Following immunization, antisera can be obtained, and if desired, polyclonal antibodies can be isolated from the serum. Monoclonal antibodies can also be produced by standard techniques, which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc. pp. 77–96 (1985)). The term "antibody" as used herein is intended to include fragments thereof, such as Fab and F(ab)$_2$.

Antibodies described herein can be used to inhibit the activity of the phosphatase described herein, particularly in vitro and in cell extracts, using methods known in the art. Additionally, antibodies can be detectably labeled, such as with a radioactive label, and used to assay for the presence of the expressed protein in a cell, such as yeast or tissue culture or a tissue sample, and can be used in an immuno-absorption process, such as an ELISA, to isolate the polypeptides or fragments thereof of the present invention or altered forms thereof. Tissue samples which can be assayed include mammalian tissues, e.g., differentiated and non-differentiated cells. Examples include bone marrow, thymus, kidney, liver, brain, pancreas, fibroblasts, epithelium, and muscle.

The novel family members of Sterile 20, C12-2bs (SEQ ID NOs. 1 and 9) and 5e.new (SEQ ID NO. 3) described herein are useful to study upstream and downstream elements in the signal transduction cascades involving these molecules, homologues of these molecules or family members. Further, SEQ ID NOs. 1, 3 or 9 or portions thereof can be used to isolate and clone homologues of these genes from other organisms such as humans, or to clone closely related family members in mouse or in other organisms such as humans. SEQ ID NOs.: 1, 3 and 9, or portions thereof can be used as probes or PCR primers. The proteins encoded by SEQ ID NOs. 2, 4 and 10 can be used in standard phosphorylation assays to discover and characterize effectors and substrates of these proteins.

These signaling molecules participate in a diverse set of events in the cell in response to many different stimuli. For example, for this family of kinases, oxidative stress can be a regulatory element. These kinases are important for ischemic, stroke, heart disease, inflammation, and cancer and are targets for drug therapeutics, both for blocking agents as well as agents that enhance kinase activity.

The present invention will now be, illustrated by the following example, which are not intended to be limiting in any way.

EXEMPLIFICATION

CLONING PUTATIVE Ste20 SERINE/THREONINE KINASES

PCR in conjunction with the primers SEQ ID NOs. 5–7 was used to amplify sequences from a murine erythroleukemia cDNA library in λgt11. In one reaction, the primer set was SEQ ID NOs. 5 and 6, and: in a separate reaction, the primer set was SEQ ID NOs. 5 and 6. In all reactions Taq polymerase was used.

Sequence alignment revealed that C12-2bs and 5e.new share homology with the Sterile 20 family of protein kinases (FIGS. 4 and 7). C12-2bs and 5e.new represent new members of the Sterile 20 family of protein kinases.

Those skilled in the art will recognize, or be able to ascertain using no more than routine experimentation, many equivalents to the specific embodiments of the invention described herein. Such equivalents are intended to be encompassed by the following claims.

What is claimed is:

1. A purified nucleic acid selected from the group consisting of: SEQ ID NO:3, a complementary sequence of SEQ ID NO:3, and a sequence having greater than about 600 bases in length wherein said sequence hybridizes to SEQ ID NO:3 or the complement of SEQ ID NO:3 under stringent conditions, wherein said purified nucleic acid encodes a serine/threonine kinase or is complementary to a sequence that encodes a serine/threonine kinase, and wherein said stringent conditions are at least as stringent as 4×SSC at 65° C.

2. A vector comprising the nucleic acid of claim 1.

3. A host cell comprising the vector of claim 2.

4. A method of producing a serine/threonine kinase comprising transfecting a host cell with the vector of claim 2, incubating the transfected cells under conditions whereby the serine/threonine kinase encoded by the vector is expressed, and isolating the kinase encoded by the vector.

5. A purified nucleic acid comprising a nucleic acid sequence encoding an amino acid sequence comprising SEQ ID NO: 4.

6. A purified nucleic acid sequence comprising SEQ ID NO: 3.

* * * * *

SEQUENCE LISTING

<160> NUMBER OF SEQ ID NOS: 10

<210> SEQ ID NO 1
<211> LENGTH: 1500
<212> TYPE: DNA
<213> ORGANISM: Mus musculus
<220> FEATURE:
<221> NAME/KEY: CDS
<222> LOCATION: (20)...(1258)

<400> SEQUENCE: 1

```
ctagtcgggc ctgccgggc atg cag aac ctg aaa gca gac cca gaa gag ctt         52
                    Met Gln Asn Leu Lys Ala Asp Pro Glu Glu Leu
                     1               5                  10 ttt acc aag cta gag aag att gga aag ggc tct ttt ggt gaa gtg ttc         100
Phe Thr Lys Leu Glu Lys Ile Gly Lys Gly Ser Phe Gly Glu Val Phe
            15                  20                  25 aaa ggc att gac aat cgg act cag aaa gtg gtg gcc ata aaa atc att         148
Lys Gly Ile Asp Asn Arg Thr Gln Lys Val Val Ala Ile Lys Ile Ile
        30                  35                  40 gat ctg gaa gaa gcc gag gac gag ata gag gac atc caa caa gag atc         196
Asp Leu Glu Glu Ala Glu Asp Glu Ile Glu Asp Ile Gln Gln Glu Ile
    45                  50                  55 aca gtg ctg agc cag tgt gac agt ccc tac gtc acc aag tac tat gga         244
Thr Val Leu Ser Gln Cys Asp Ser Pro Tyr Val Thr Lys Tyr Tyr Gly
 60                  65                  70                  75 tcc tat ctc aag gat act aag ttg tgg ata atc atg gag tat ctt ggt         292
Ser Tyr Leu Lys Asp Thr Lys Leu Trp Ile Ile Met Glu Tyr Leu Gly
                80                  85                  90 gga ggc tct gcc ctg gat ctg tta gag cct ggc cct tta gat gaa att         340
Gly Gly Ser Ala Leu Asp Leu Leu Glu Pro Gly Pro Leu Asp Glu Ile
            95                 100                 105 cag att gca acc ata tta cga gaa att ctg aaa gga ctt gat tat cta         388
Gln Ile Ala Thr Ile Leu Arg Glu Ile Leu Lys Gly Leu Asp Tyr Leu
        110                 115                 120 cac tcg gag aag aaa att cac aga gat att aaa gag gcc aat gtt ctg         436
His Ser Glu Lys Lys Ile His Arg Asp Ile Lys Glu Ala Asn Val Leu
    125                 130                 135 ctc tct gaa cat gga gag gtg aag ctg gca gac ttt gga gtg gcc ggc         484
Leu Ser Glu His Gly Glu Val Lys Leu Ala Asp Phe Gly Val Ala Gly
140                 145                 150                 155 cag ctg acg gat acc cag atc aaa agg aac acc ttc gtg ggt acc ccc         532
Gln Leu Thr Asp Thr Gln Ile Lys Arg Asn Thr Phe Val Gly Thr Pro
                160                 165                 170 ttc tgg atg gcg ccg gag gtc atc aag cag tca gcc tac gac tca aag         580
Phe Trp Met Ala Pro Glu Val Ile Lys Gln Ser Ala Tyr Asp Ser Lys
            175                 180                 185 gca gac atc tgg tcc ctt ggc atc acc gca ata gaa ctg gca aaa gga         628
Ala Asp Ile Trp Ser Leu Gly Ile Thr Ala Ile Glu Leu Ala Lys Gly
        190                 195                 200 gag cca cca cat tct gag ctg cac ccc atg aag gtg tta ttc ctc atc         676
Glu Pro Pro His Ser Glu Leu His Pro Met Lys Val Leu Phe Leu Ile
    205                 210                 215 cca aag aac aac cct ccc aca ctg gaa ggg aac tac agc aaa ccc ctc         724
Pro Lys Asn Asn Pro Pro Thr Leu Glu Gly Asn Tyr Ser Lys Pro Leu
220                 225                 230                 235 aag gag ttc gtg gag gcc tgc ctg aac aag gag ccc agc ttt agg ccc         772
Lys Glu Phe Val Glu Ala Cys Leu Asn Lys Glu Pro Ser Phe Arg Pro
                240                 245                 250
```

```
act gct aag gaa tta ttg aag cac aaa ttc ata atc cgc aat gca aag      820
Thr Ala Lys Glu Leu Leu Lys His Lys Phe Ile Ile Arg Asn Ala Lys
        255                 260                 265 aaa acg tcc tac ttg acc gag ctt atc gac agg tac aag agg tgg aag      868
Lys Thr Ser Tyr Leu Thr Glu Leu Ile Asp Arg Tyr Lys Arg Trp Lys
            270                 275                 280 gcg gag cag agc cac gag gac tcc agc tcg gag gac tct gac gtg gag      916
Ala Glu Gln Ser His Glu Asp Ser Ser Ser Glu Asp Ser Asp Val Glu
285                 290                 295 aca gat ggc cag gcg tct gga ggc agc gac tct ggg gac tgg atc ttc      964
Thr Asp Gly Gln Ala Ser Gly Gly Ser Asp Ser Gly Asp Trp Ile Phe
300                 305                 310                 315 act atc cgg gag aaa gat ccc aag aat ctg gag aac gga act ctt cag     1012
Thr Ile Arg Glu Lys Asp Pro Lys Asn Leu Glu Asn Gly Thr Leu Gln
                320                 325                 330 ctc tcg gac ttg gaa aga aat aag atg aaa gat atc cca aag aag cct     1060
Leu Ser Asp Leu Glu Arg Asn Lys Met Lys Asp Ile Pro Lys Lys Pro
            335                 340                 345 ttc tct cag tgt ttt atc cca caa tca ttt ctc ctc ctg ttt tgc gga     1108
Phe Ser Gln Cys Phe Ile Pro Gln Ser Phe Leu Leu Leu Phe Cys Gly
        350                 355                 360 gct gaa aag aca aag agc caa ggc atg cgg agg gaa ctt ggg gtc aat     1156
Ala Glu Lys Thr Lys Ser Gln Gly Met Arg Arg Glu Leu Gly Val Asn
365                 370                 375 aga aga gct gcg ggg gag cca tct act tgg cgg aag agg cct gcc ctg     1204
Arg Arg Ala Ala Gly Glu Pro Ser Thr Trp Arg Lys Arg Pro Ala Leu
380                 385                 390                 395 gga tct cag aca cta tgg tgg cac agc ttg tgc agc ggc tgc aga gat     1252
Gly Ser Gln Thr Leu Trp Trp His Ser Leu Cys Ser Gly Cys Arg Asp
                400                 405                 410 att ctc tgagtggcgg aggagcctca gcgcactgaa ggcccatggc gcccgggttg     1308
Ile Leu gtttttcctt tcttcttcat cttccttctt tttaaaagtc aacgagagcc tttgccgact    1368
ctgcgaagag gtgtcacgga ggggcccacc cgccctccca tagcgccggc acctgtccct    1428
cgtgccgaat tcctgcagcc cggggatcc actagttcta gagcggccgc caccgcggtg     1488
gagctccagt tt                                                        1500

<210> SEQ ID NO 2
<211> LENGTH: 413
<212> TYPE: PRT
<213> ORGANISM: Mus musculus

<400> SEQUENCE: 2

Met Gln Asn Leu Lys Ala Asp Pro Glu Glu Leu Phe Thr Lys Leu Glu
1               5                   10                  15

Lys Ile Gly Lys Gly Ser Phe Gly Glu Val Phe Lys Gly Ile Asp Asn
            20                  25                  30

Arg Thr Gln Lys Val Val Ala Ile Lys Ile Ile Asp Leu Glu Glu Ala
        35                  40                  45

Glu Asp Glu Ile Glu Asp Ile Gln Gln Glu Ile Thr Val Leu Ser Gln
    50                  55                  60

Cys Asp Ser Pro Tyr Val Thr Lys Tyr Tyr Gly Ser Tyr Leu Lys Asp
65                  70                  75                  80

Thr Lys Leu Trp Ile Ile Met Glu Tyr Leu Gly Gly Gly Ser Ala Leu
                85                  90                  95

Asp Leu Leu Glu Pro Gly Pro Leu Asp Glu Ile Gln Ile Ala Thr Ile
            100                 105                 110
```

-continued

```
Leu Arg Glu Ile Leu Lys Gly Leu Asp Tyr Leu His Ser Glu Lys Lys
        115                 120                 125

Ile His Arg Asp Ile Lys Glu Ala Asn Val Leu Leu Ser Glu His Gly
    130                 135                 140

Glu Val Lys Leu Ala Asp Phe Gly Val Ala Gly Gln Leu Thr Asp Thr
145                 150                 155                 160

Gln Ile Lys Arg Asn Thr Phe Val Gly Thr Pro Phe Trp Met Ala Pro
                165                 170                 175

Glu Val Ile Lys Gln Ser Ala Tyr Asp Ser Lys Ala Asp Ile Trp Ser
            180                 185                 190

Leu Gly Ile Thr Ala Ile Glu Leu Ala Lys Gly Glu Pro Pro His Ser
        195                 200                 205

Glu Leu His Pro Met Lys Val Leu Phe Leu Ile Pro Lys Asn Asn Pro
    210                 215                 220

Pro Thr Leu Glu Gly Asn Tyr Ser Lys Pro Leu Lys Glu Phe Val Glu
225                 230                 235                 240

Ala Cys Leu Asn Lys Glu Pro Ser Phe Arg Pro Thr Ala Lys Glu Leu
                245                 250                 255

Leu Lys His Lys Phe Ile Ile Arg Asn Ala Lys Lys Thr Ser Tyr Leu
            260                 265                 270

Thr Glu Leu Ile Asp Arg Tyr Lys Arg Trp Lys Ala Glu Gln Ser His
        275                 280                 285

Glu Asp Ser Ser Glu Asp Ser Asp Val Glu Thr Asp Gly Gln Ala
    290                 295                 300

Ser Gly Gly Ser Asp Ser Gly Asp Trp Ile Phe Thr Ile Arg Glu Lys
305                 310                 315                 320

Asp Pro Lys Asn Leu Glu Asn Gly Thr Leu Gln Leu Ser Asp Leu Glu
                325                 330                 335

Arg Asn Lys Met Lys Asp Ile Pro Lys Pro Phe Ser Gln Cys Phe
            340                 345                 350

Ile Pro Gln Ser Phe Leu Leu Leu Phe Cys Gly Ala Glu Lys Thr Lys
        355                 360                 365

Ser Gln Gly Met Arg Arg Glu Leu Gly Val Asn Arg Arg Ala Ala Gly
    370                 375                 380

Glu Pro Ser Thr Trp Arg Lys Arg Pro Ala Leu Gly Ser Gln Thr Leu
385                 390                 395                 400

Trp Trp His Ser Leu Cys Ser Gly Cys Arg Asp Ile Leu
                405                 410

<210> SEQ ID NO 3
<211> LENGTH: 1979
<212> TYPE: DNA
<213> ORGANISM: Mus musculus
<220> FEATURE:
<221> NAME/KEY: CDS
<222> LOCATION: (220)...(1467)

<400> SEQUENCE: 3
ggcacgagcc caggtcccag gcaccgccac aggtcaagcc ctgcattcag gaaagagagc     60
aacactgcag ttagccaaaa gccaggcagg cgagcggcat agaggcctcg atcgagaagc    120
ccggtagagc tgcagagata cctccgtagg aggagccagt ctctgccgga ggcgccaccg    180
ccaccaccgc agaagcagcg cgaagtagca gtcgccacc atg gcc cac tca ccg       234
                                          Met Ala His Ser Pro
                                            1               5
```

-continued

| | |
|---|---|
| gtg gct gtt caa gtg cct ggg atg cag aat aat ata gca gat cca gaa<br>Val Ala Val Gln Val Pro Gly Met Gln Asn Asn Ile Ala Asp Pro Glu<br>          10                    15                20 | 282 |
| gaa ctg ttc aca aaa tta gag cgc att gga aaa ggc tcc ttt gga gaa<br>Glu Leu Phe Thr Lys Leu Glu Arg Ile Gly Lys Gly Ser Phe Gly Glu<br>              25                  30                35 | 330 |
| gtt ttc aaa gga att gat aac cgt act cag caa gtg gtt gca att aaa<br>Val Phe Lys Gly Ile Asp Asn Arg Thr Gln Gln Val Val Ala Ile Lys<br>          40                    45                  50 | 378 |
| atc att gac ctt gag gaa gct gag gat gaa ata gaa gac atc caa caa<br>Ile Ile Asp Leu Glu Glu Ala Glu Asp Glu Ile Glu Asp Ile Gln Gln<br>55                    60                    65 | 426 |
| gaa ata act gtt ttg agt cag tgc gac agc tca tat gta aca aaa tac<br>Glu Ile Thr Val Leu Ser Gln Cys Asp Ser Ser Tyr Val Thr Lys Tyr<br>70                    75                  80                85 | 474 |
| tat ggg tcc tat tta aag ggt tca aaa cta tgg ata ata atg gaa tac<br>Tyr Gly Ser Tyr Leu Lys Gly Ser Lys Leu Trp Ile Ile Met Glu Tyr<br>              90                  95                100 | 522 |
| cta ggt gga ggt tca gca ttg gat ctt ctg cgt gct ggt cca ttt gat<br>Leu Gly Gly Gly Ser Ala Leu Asp Leu Leu Arg Ala Gly Pro Phe Asp<br>              105                110              115 | 570 |
| gag ttc cag att gcc acc atg ctc aag gag att ttg aaa ggt ctg gac<br>Glu Phe Gln Ile Ala Thr Met Leu Lys Glu Ile Leu Lys Gly Leu Asp<br>          120                125                130 | 618 |
| tat cta cat tct gaa aag aaa atc cac cga gac att aaa gct gcc aac<br>Tyr Leu His Ser Glu Lys Lys Ile His Arg Asp Ile Lys Ala Ala Asn<br>     135                    140                145 | 666 |
| gtc ttg ctt tca gaa caa ggt gat gtt aaa ctg gct gac ttt gga gtt<br>Val Leu Leu Ser Glu Gln Gly Asp Val Lys Leu Ala Asp Phe Gly Val<br>150                    155                160              165 | 714 |
| gct ggc cag ctg aca gat aca caa atc aaa aga aac acc ttc gta ggg<br>Ala Gly Gln Leu Thr Asp Thr Gln Ile Lys Arg Asn Thr Phe Val Gly<br>              170                175              180 | 762 |
| act ccg ttt tgg atg gct cct gaa gtt att caa cag tca gct tat gac<br>Thr Pro Phe Trp Met Ala Pro Glu Val Ile Gln Gln Ser Ala Tyr Asp<br>          185                190                195 | 810 |
| tct aaa gct gac ata tgg tct ttg gga att act gct att gaa ctt gcc<br>Ser Lys Ala Asp Ile Trp Ser Leu Gly Ile Thr Ala Ile Glu Leu Ala<br>          200                205                210 | 858 |
| aag gga gag cct ccg aat tct gac atg cat cca atg aga gtt ctg ttt<br>Lys Gly Glu Pro Pro Asn Ser Asp Met His Pro Met Arg Val Leu Phe<br>     215                    220                225 | 906 |
| ctt att cca aaa aac aac cct cca act ctt att gga gac ttt act aag<br>Leu Ile Pro Lys Asn Asn Pro Pro Thr Leu Ile Gly Asp Phe Thr Lys<br>230                    235              240              245 | 954 |
| tct ttc aag gag ttt att gat gct tgc ctg aat aaa gac ccg tca ttt<br>Ser Phe Lys Glu Phe Ile Asp Ala Cys Leu Asn Lys Asp Pro Ser Phe<br>          250                255                260 | 1002 |
| cgt cct aca gct aaa gaa ctt ttg aag cat aag ttc atc gta aaa aat<br>Arg Pro Thr Ala Lys Glu Leu Leu Lys His Lys Phe Ile Val Lys Asn<br>          265                270                275 | 1050 |
| tca aag aag act tct tat ctg act gaa ttg atc gat cga ttt aag aga<br>Ser Lys Lys Thr Ser Tyr Leu Thr Glu Leu Ile Asp Arg Phe Lys Arg<br>          280                285                290 | 1098 |
| tgg aag gca gaa ggc cac agt gat gag gaa tct gat tcc gag ggc tct<br>Trp Lys Ala Glu Gly His Ser Asp Glu Glu Ser Asp Ser Glu Gly Ser<br>     295                    300                305 | 1146 |
| gac tcg gaa tcc agc agc agg gaa agt aac cct cac cct gaa tgg agt<br>Asp Ser Glu Ser Ser Ser Arg Glu Ser Asn Pro His Pro Glu Trp Ser<br>310                    315              320              325 | 1194 |

```
ttc acc act gtg cgt aag aag cct gat cca aag aaa ctg cag aat ggg    1242
Phe Thr Thr Val Arg Lys Lys Pro Asp Pro Lys Lys Leu Gln Asn Gly
                330                 335                 340 gaa gag caa gat ctt gtg caa acc ttg agc tgt ttg tct atg ata atc    1290
Glu Glu Gln Asp Leu Val Gln Thr Leu Ser Cys Leu Ser Met Ile Ile
            345                 350                 355 aca cct gca ttt gcc gaa ctt aaa cag cag gac gag aat aat gcg agt    1338
Thr Pro Ala Phe Ala Glu Leu Lys Gln Gln Asp Glu Asn Asn Ala Ser
        360                 365                 370 cga aac cag gca att gaa gaa ctt gag aaa agt att gct gtg gct gaa    1386
Arg Asn Gln Ala Ile Glu Glu Leu Glu Lys Ser Ile Ala Val Ala Glu
    375                 380                 385 acc gcc tgt cct ggc atc aca gat aag atg gtg aag aaa cta atc gaa    1434
Thr Ala Cys Pro Gly Ile Thr Asp Lys Met Val Lys Lys Leu Ile Glu
390                 395                 400                 405 aaa ttt caa aag tgt tct gcg gat gaa tcc cct taagaaatct gttgtcatta    1487
Lys Phe Gln Lys Cys Ser Ala Asp Glu Ser Pro
                410                 415 cttttggctt ctgtttcatg tggaccagga gaaacccacc aaagctatgt caaccttata    1547
aatgcttaac tcatgagctc catgtgcctt ttggatcttt gccacattga agatttagag    1607
gaagctatta aactattttg tgatggtgat tatcattttg tattttaaag agattatttt    1667
gtaaggaata attttaatac tatagttttg ccggtattgt agtaaatgct gagatacagg    1727
ttttttgttt tttgttttt aattttaggt accattattt cttatgttca tggaatgaat    1787
actgtttggt ttggaatctt tagttaactg tatactcata acatacagg tctttcaaag    1847 tcatcctaac tattaaatgt ttgtaaatca tcaagcttca aaaagcattc tttttccccc    1907
acacaagtat attctaaaaa gactatttgt aatgaggtgg aagtaagtaa taccttctta    1967
aaacctcgtg cc                                                        1979

<210> SEQ ID NO 4
<211> LENGTH: 416
<212> TYPE: PRT
<213> ORGANISM: Mus musculus

<400> SEQUENCE: 4

Met Ala His Ser Pro Val Ala Val Gln Val Pro Gly Met Gln Asn Asn
1               5                   10                  15

Ile Ala Asp Pro Glu Glu Leu Phe Thr Lys Leu Glu Arg Ile Gly Lys
            20                  25                  30

Gly Ser Phe Gly Glu Val Phe Lys Gly Ile Asp Asn Arg Thr Gln Gln
        35                  40                  45

Val Val Ala Ile Lys Ile Ile Asp Leu Glu Glu Ala Glu Asp Glu Ile
    50                  55                  60

Glu Asp Ile Gln Gln Glu Ile Thr Val Leu Ser Gln Cys Asp Ser Ser
65                  70                  75                  80

Tyr Val Thr Lys Tyr Tyr Gly Ser Tyr Leu Lys Gly Ser Lys Leu Trp
                85                  90                  95

Ile Ile Met Glu Tyr Leu Gly Gly Gly Ser Ala Leu Asp Leu Leu Arg
            100                 105                 110

Ala Gly Pro Phe Asp Glu Phe Gln Ile Ala Thr Met Leu Lys Glu Ile
        115                 120                 125

Leu Lys Gly Leu Asp Tyr Leu His Ser Glu Lys Lys Ile His Arg Asp
    130                 135                 140

Ile Lys Ala Ala Asn Val Leu Leu Ser Glu Gln Gly Asp Val Lys Leu
```

```
                145                 150                 155                 160
Ala Asp Phe Gly Val Ala Gly Gln Leu Thr Asp Thr Gln Ile Lys Arg
                    165                 170                 175
Asn Thr Phe Val Gly Thr Pro Phe Trp Met Ala Pro Glu Val Ile Gln
                180                 185                 190
Gln Ser Ala Tyr Asp Ser Lys Ala Asp Ile Trp Ser Leu Gly Ile Thr
                195                 200                 205
Ala Ile Glu Leu Ala Lys Gly Glu Pro Pro Asn Ser Asp Met His Pro
    210                 215                 220
Met Arg Val Leu Phe Leu Ile Pro Lys Asn Asn Pro Pro Thr Leu Ile
225                 230                 235                 240
Gly Asp Phe Thr Lys Ser Phe Lys Glu Phe Ile Asp Ala Cys Leu Asn
                    245                 250                 255
Lys Asp Pro Ser Phe Arg Pro Thr Ala Lys Glu Leu Leu Lys His Lys
                260                 265                 270
Phe Ile Val Lys Asn Ser Lys Lys Thr Ser Tyr Leu Thr Glu Leu Ile
            275                 280                 285
Asp Arg Phe Lys Arg Trp Lys Ala Glu Gly His Ser Asp Glu Ser
        290                 295                 300
Asp Ser Glu Gly Ser Asp Ser Glu Ser Ser Arg Glu Ser Asn Pro
305                 310                 315                 320
His Pro Glu Trp Ser Phe Thr Thr Val Arg Lys Lys Pro Asp Pro Lys
                    325                 330                 335
Lys Leu Gln Asn Gly Glu Gln Asp Leu Val Gln Thr Leu Ser Cys
                340                 345                 350
Leu Ser Met Ile Ile Thr Pro Ala Phe Ala Glu Leu Lys Gln Gln Asp
            355                 360                 365
Glu Asn Asn Ala Ser Arg Asn Gln Ala Ile Glu Leu Glu Lys Ser
    370                 375                 380
Ile Ala Val Ala Glu Thr Ala Cys Pro Gly Ile Thr Asp Lys Met Val
385                 390                 395                 400
Lys Lys Leu Ile Glu Lys Phe Gln Lys Cys Ser Ala Asp Glu Ser Pro
                    405                 410                 415

<210> SEQ ID NO 5
<211> LENGTH: 38
<212> TYPE: DNA
<213> ORGANISM: Artificial Sequence
<220> FEATURE:
<223> OTHER INFORMATION: Primer
<221> NAME/KEY: misc_feature
<222> LOCATION: 15,27,30
<223> OTHER INFORMATION: n = A,T,C or G

<400> SEQUENCE: 5
ataggatccc aymgngawat haarggngcn aayathyt                              38

<210> SEQ ID NO 6
<211> LENGTH: 27
<212> TYPE: DNA
<213> ORGANISM: Artificial Sequence
<220> FEATURE:
<223> OTHER INFORMATION: Primer
<221> NAME/KEY: misc_feature
<222> LOCATION: 13,16
<223> OTHER INFORMATION: n = A,T,C or G

<400> SEQUENCE: 6
tcggaattcy tcnggngcca tccarta                                         27
```

<210> SEQ ID NO 7
<211> LENGTH: 27
<212> TYPE: DNA
<213> ORGANISM: Artificial Sequence
<220> FEATURE:
<223> OTHER INFORMATION: Primer
<221> NAME/KEY: misc_feature
<222> LOCATION: 13,16
<223> OTHER INFORMATION: n = A,T,C or G

<400> SEQUENCE: 7
tcggaattcy tcnggngcca tccaraa                                          27

<210> SEQ ID NO 8
<211> LENGTH: 487
<212> TYPE: PRT
<213> ORGANISM: Homo sapiens

<400> SEQUENCE: 8

```
Met Glu Thr Val Gln Leu Arg Asn Pro Pro Arg Arg Gln Leu Lys Lys
 1               5                  10                  15

Leu Asp Glu Asp Ser Leu Thr Lys Gln Pro Glu Glu Val Phe Asp Val
            20                  25                  30

Leu Glu Lys Leu Gly Glu Gly Ser Tyr Gly Ser Val Tyr Lys Ala Ile
        35                  40                  45

His Lys Glu Thr Gly Gln Ile Val Ala Ile Lys Gln Val Pro Val Glu
    50                  55                  60

Ser Asp Leu Gln Glu Ile Ile Lys Glu Ile Ser Ile Met Gln Gln Cys
65                  70                  75                  80

Asp Ser Pro His Val Val Lys Tyr Tyr Gly Ser Tyr Phe Lys Asn Thr
                85                  90                  95

Asp Leu Trp Ile Val Met Glu Tyr Cys Gly Ala Gly Ser Val Ser Asp
            100                 105                 110

Ile Ile Arg Leu Arg Asn Lys Thr Leu Thr Glu Asp Glu Ile Ala Thr
        115                 120                 125

Ile Leu Gln Ser Thr Leu Lys Gly Leu Glu Tyr Leu His Phe Met Arg
    130                 135                 140

Gln Ile His Arg Asp Ile Lys Ala Gly Asn Ile Leu Leu Asn Thr Glu
145                 150                 155                 160

Gly His Ala Lys Leu Ala Asp Phe Gly Val Ala Gly Gln Leu Thr Asp
                165                 170                 175

Thr Met Ala Lys Arg Asn Thr Val Ile Gly Thr Pro Phe Trp Met Ala
            180                 185                 190

Pro Glu Val Ile Gln Glu Ile Gly Tyr His Cys Val Ala Asp Ile Trp
        195                 200                 205

Ser Leu Gly Ile Thr Ala Ile Glu Met Ala Glu Gly Lys Pro Pro Tyr
    210                 215                 220

Ala Asp Ile His Pro Met Arg Ala Ile Phe Met Ile Pro Thr Asn Pro
225                 230                 235                 240

Pro Pro Thr Phe Arg Lys Pro Glu Leu Trp Ser Asp Asn Phe Met Asp
                245                 250                 255

Phe Val Lys Gln Cys Leu Val Lys Ser Pro Glu Gln Arg Ala Thr Ala
            260                 265                 270

Thr Gln Leu Leu Gln His Pro Phe Val Lys Ser Ala Lys Gly Val Ser
        275                 280                 285

Ile Leu Arg Asp Leu Ile Asn Glu Ala Met Asp Val Lys Leu Lys Arg
```

```
                    290                     295                     300

Gln Glu Ala Gln Gln Arg Glu Val Asp Gln Asp Asp Glu Asn Ser
305                 310                 315                 320

Glu Glu Asp Glu Met Asp Ser Gly Thr Met Val Arg Thr Ala Gly Asp
                325                 330                 335

Glu Met Gly Thr Val Arg Val Ala Ser Thr Met Ser Gly Gly Ala Asn
            340                 345                 350

Thr Met Ile Glu His Gly Asp Thr Leu Pro Ser Gln Leu Gly Thr Met
        355                 360                 365

Val Ile Asn Thr Glu Asp Glu Glu Gly Thr Met Lys Arg Arg
370                 375                 380

Asp Glu Thr Met Gln Pro Ala Lys Pro Ser Phe Leu Glu Tyr Phe Glu
385                 390                 395                 400

Gln Lys Glu Lys Glu Asn Gln Ile Asn Ser Phe Gly Lys Asn Val Ser
                405                 410                 415

Gly Ser Leu Lys Asn Ser Ser Asp Trp Lys Ile Pro Gln Asp Gly Asp
            420                 425                 430

Tyr Glu Phe Leu Lys Ser Trp Thr Val Glu Asp Leu Gln Lys Arg Leu
        435                 440                 445

Leu Ala Leu Asp Pro Met Met Glu Gln Glu Met Glu Glu Ile Arg Gln
450                 455                 460

Lys Tyr Arg Ser Lys Arg Gln Pro Ile Leu Asp Ala Ile Glu Ala Lys
465                 470                 475                 480

Lys Arg Arg Gln Gln Asn Phe
                485

<210> SEQ ID NO 9
<211> LENGTH: 1744
<212> TYPE: DNA
<213> ORGANISM: Mus musculus
<220> FEATURE:
<221> NAME/KEY: CDS
<222> LOCATION: (302)...(1597)

<400> SEQUENCE: 9
ggcacgagcc agcgctcgcg ggcccaggcc gcccggctcg acctgagcac cgcggcggcg      60
cagcgacggg atccctggag aagcagccgc agtctcgaga cgtccccgc gcccccact     120 gcccgcccca ggctcagtgt atggggccgg ggccgccaa ccttcgttga gaccgtcccc     180
ggggtgcggt ggcctcgggc tccagagccc gccccgccac ccgagggctg cgcgcggccc     240
cgggcctgct cgccgcgcgg ctccgcgcgt cccgggccag gaagtggcgg cgccgagcgc     300 c atg gcc cac tcc ccg gtg cag tcg ggc ctg ccg ggc atg cag aac ctg     349
  Met Ala His Ser Pro Val Gln Ser Gly Leu Pro Gly Met Gln Asn Leu
    1               5                  10                  15 aaa gca gac cca gaa gag ctt ttt acc aag cta gag aag att gga aag     397
Lys Ala Asp Pro Glu Glu Leu Phe Thr Lys Leu Glu Lys Ile Gly Lys
            20                  25                  30 ggc tct ttt ggt gaa gtg ttc aaa ggc att gac aat cgg act cag aaa     445
Gly Ser Phe Gly Glu Val Phe Lys Gly Ile Asp Asn Arg Thr Gln Lys
        35                  40                  45 gtg gtg gcc ata aaa atc att gat ctg gaa gaa gcc gag gac gag ata     493
Val Val Ala Ile Lys Ile Ile Asp Leu Glu Glu Ala Glu Asp Glu Ile
    50                  55                  60 gag gac atc caa caa gag atc aca gtg ctg agc cag tgt gac agt ccc     541
Glu Asp Ile Gln Gln Glu Ile Thr Val Leu Ser Gln Cys Asp Ser Pro
65                  70                  75                  80
```

-continued

| | |
|---|---|
| tac gtc acc aag tac tat gga tcc tat ctc aag gat act aag ttg tgg<br>Tyr Val Thr Lys Tyr Tyr Gly Ser Tyr Leu Lys Asp Thr Lys Leu Trp<br>              85                    90                  95 | 589 |
| ata atc atg gag tat ctt ggt gga ggc tct gcc ctg gat ctg tta gag<br>Ile Ile Met Glu Tyr Leu Gly Gly Gly Ser Ala Leu Asp Leu Leu Glu<br>          100                    105                110 | 637 |
| cct ggc cct tta gat gaa att cag att gca acc ata tta cga gaa att<br>Pro Gly Pro Leu Asp Glu Ile Gln Ile Ala Thr Ile Leu Arg Glu Ile<br>        115                    120                125 | 685 |
| ctg aaa gga ctt gat tat cta cac tcg gag aag aaa att cac aga gat<br>Leu Lys Gly Leu Asp Tyr Leu His Ser Glu Lys Lys Ile His Arg Asp<br>130                    135                    140 | 733 |
| att aaa gcg gcc aat gtt ctg ctc tct gaa cat gga gag gtg aag ctg<br>Ile Lys Ala Ala Asn Val Leu Leu Ser Glu His Gly Glu Val Lys Leu<br>145                    150                    155                160 | 781 |
| gca gac ttt gga gtg gcc ggc cag ctg acg gat acc cag atc aaa agg<br>Ala Asp Phe Gly Val Ala Gly Gln Leu Thr Asp Thr Gln Ile Lys Arg<br>              165                    170                175 | 829 |
| aac acc ttc gtg ggt acc ccc ttc tgg atg gcg ccg gag gtc atc aag<br>Asn Thr Phe Val Gly Thr Pro Phe Trp Met Ala Pro Glu Val Ile Lys<br>          180                    185                190 | 877 |
| cag tca gcc tac gac tca aag gca gac atc tgg tcc ctt ggc atc acc<br>Gln Ser Ala Tyr Asp Ser Lys Ala Asp Ile Trp Ser Leu Gly Ile Thr<br>        195                    200                205 | 925 |
| gca ata gaa ctg gcc aaa gga gag cca cca cat tct gag ctg cac ccc<br>Ala Ile Glu Leu Ala Lys Gly Glu Pro Pro His Ser Glu Leu His Pro<br>210                    215                    220 | 973 |
| atg aag gtg tta ttc ctc atc cca aag aac aac cct ccc aca ctg gaa<br>Met Lys Val Leu Phe Leu Ile Pro Lys Asn Asn Pro Pro Thr Leu Glu<br>225                    230                    235                240 | 1021 |
| ggg aac tac agc aaa ccc ctc aag gag ttc gtg gag gcc tgc ctg aac<br>Gly Asn Tyr Ser Lys Pro Leu Lys Glu Phe Val Glu Ala Cys Leu Asn<br>              245                    250                255 | 1069 |
| aag gag ccc agc ttt agg ccc act gct aag gaa tta ttg aag cac aaa<br>Lys Glu Pro Ser Phe Arg Pro Thr Ala Lys Glu Leu Leu Lys His Lys<br>        260                    265                270 | 1117 |
| ttc ata atc cgc aat gca aag aaa acg tcc tac ttg acc gag ctt atc<br>Phe Ile Ile Arg Asn Ala Lys Lys Thr Ser Tyr Leu Thr Glu Leu Ile<br>          275                    280                285 | 1165 |
| gac agg tac aag agg tgg aag gcg gag cag agc cac gag gac tcc agc<br>Asp Arg Tyr Lys Arg Trp Lys Ala Glu Gln Ser His Glu Asp Ser Ser<br>290                    295                    300 | 1213 |
| tcg gag gac tct gac gtg gag aca gat ggc cag gcg tct gga ggc agc<br>Ser Glu Asp Ser Asp Val Glu Thr Asp Gly Gln Ala Ser Gly Gly Ser<br>305                    310                    315                320 | 1261 |
| gac tct ggg gac tgg atc ttc act atc cgg gag aaa gat ccc aag aat<br>Asp Ser Gly Asp Trp Ile Phe Thr Ile Arg Glu Lys Asp Pro Lys Asn<br>              325                    330                335 | 1309 |
| ctg gag aac gga act ctt cag ctc tcg gac ttg gaa aga aat aag atg<br>Leu Glu Asn Gly Thr Leu Gln Leu Ser Asp Leu Glu Arg Asn Lys Met<br>              340                    345                350 | 1357 |
| aaa gat atc cca aag agg cct ttc tct cag tgt tta tcc aca atc att<br>Lys Asp Ile Pro Lys Arg Pro Phe Ser Gln Cys Leu Ser Thr Ile Ile<br>        355                    360                365 | 1405 |
| tct cct ctg ttt gcg gag ctg aaa gag aag agc cag gca tgc gga ggg<br>Ser Pro Leu Phe Ala Glu Leu Lys Glu Lys Ser Gln Ala Cys Gly Gly<br>370                    375                    380 | 1453 |
| aac ttg ggg tca ata gaa gag ctg cgg gga gcc atc tac ttg gcg gaa<br>Asn Leu Gly Ser Ile Glu Glu Leu Arg Gly Ala Ile Tyr Leu Ala Glu<br>385                    390                    395                400 | 1501 |

-continued

```
gag gcc tgc cct ggg atc tca gac act atg gtg gca cag ctt gtg cag      1549
Glu Ala Cys Pro Gly Ile Ser Asp Thr Met Val Ala Gln Leu Val Gln
            405                 410                 415 cgg ctg cag aga tat tct ctg agt ggc gga gga gcc tca gcg cac tga      1597
Arg Leu Gln Arg Tyr Ser Leu Ser Gly Gly Gly Ala Ser Ala His *
        420                 425                 430 aggcccatgg cgcccgggtt ggttttcct ttcttcttca tcttccttct ttttaaaagt     1657
caacgagagc ctttgccgac tctgcgaaga ggtgtcacgg aggggcccac ccgccctccc    1717
atagcgccgg cacctgtccc tcgtgcc                                        1744
```

<210> SEQ ID NO 10
<211> LENGTH: 431
<212> TYPE: PRT
<213> ORGANISM: Mus musculus

<400> SEQUENCE: 10

```
Met Ala His Ser Pro Val Gln Ser Gly Leu Pro Gly Met Gln Asn Leu
 1               5                  10                  15

Lys Ala Asp Pro Glu Glu Leu Phe Thr Lys Leu Glu Lys Ile Gly Lys
             20                  25                  30

Gly Ser Phe Gly Glu Val Phe Lys Gly Ile Asp Asn Arg Thr Gln Lys
         35                  40                  45

Val Val Ala Ile Lys Ile Ile Asp Leu Glu Glu Ala Glu Asp Glu Ile
 50                  55                  60

Glu Asp Ile Gln Gln Glu Ile Thr Val Leu Ser Gln Cys Asp Ser Pro
 65                  70                  75                  80

Tyr Val Thr Lys Tyr Tyr Gly Ser Tyr Leu Lys Asp Thr Lys Leu Trp
                 85                  90                  95

Ile Ile Met Glu Tyr Leu Gly Gly Gly Ser Ala Leu Asp Leu Leu Glu
            100                 105                 110

Pro Gly Pro Leu Asp Glu Ile Gln Ile Ala Thr Ile Leu Arg Glu Ile
        115                 120                 125

Leu Lys Gly Leu Asp Tyr Leu His Ser Glu Lys Lys Ile His Arg Asp
    130                 135                 140

Ile Lys Ala Ala Asn Val Leu Leu Ser Glu His Gly Glu Val Lys Leu
145                 150                 155                 160

Ala Asp Phe Gly Val Ala Gly Gln Leu Thr Asp Thr Gln Ile Lys Arg
                165                 170                 175

Asn Thr Phe Val Gly Thr Pro Phe Trp Met Ala Pro Glu Val Ile Lys
            180                 185                 190

Gln Ser Ala Tyr Asp Ser Lys Ala Asp Ile Trp Ser Leu Gly Ile Thr
        195                 200                 205

Ala Ile Glu Leu Ala Lys Gly Glu Pro Pro His Ser Glu Leu His Pro
    210                 215                 220

Met Lys Val Leu Phe Leu Ile Pro Lys Asn Asn Pro Pro Thr Leu Glu
225                 230                 235                 240

Gly Asn Tyr Ser Lys Pro Leu Lys Glu Phe Val Glu Ala Cys Leu Asn
                245                 250                 255

Lys Glu Pro Ser Phe Arg Pro Thr Ala Lys Glu Leu Leu Lys His Lys
            260                 265                 270

Phe Ile Ile Arg Asn Ala Lys Lys Thr Ser Tyr Leu Thr Glu Leu Ile
        275                 280                 285

Asp Arg Tyr Lys Arg Trp Lys Ala Glu Gln Ser His Glu Asp Ser Ser
    290                 295                 300
```

-continued

```
Ser Glu Asp Ser Asp Val Glu Thr Asp Gly Gln Ala Ser Gly Gly Ser
305                 310                 315                 320

Asp Ser Gly Asp Trp Ile Phe Thr Ile Arg Glu Lys Asp Pro Lys Asn
            325                 330                 335

Leu Glu Asn Gly Thr Leu Gln Leu Ser Asp Leu Glu Arg Asn Lys Met
            340                 345                 350

Lys Asp Ile Pro Lys Arg Pro Phe Ser Gln Cys Leu Ser Thr Ile Ile
            355                 360                 365

Ser Pro Leu Phe Ala Glu Leu Lys Glu Lys Ser Gln Ala Cys Gly Gly
        370                 375                 380

Asn Leu Gly Ser Ile Glu Glu Leu Arg Gly Ala Ile Tyr Leu Ala Glu
385                 390                 395                 400

Glu Ala Cys Pro Gly Ile Ser Asp Thr Met Val Ala Gln Leu Val Gln
            405                 410                 415

Arg Leu Gln Arg Tyr Ser Leu Ser Gly Gly Gly Ala Ser Ala His
            420                 425                 430
```